United States Patent [19]

Singh

[11] Patent Number: 4,584,012
[45] Date of Patent: Apr. 22, 1986

[54] 1-PHENYLTHIO-1-CYCLOPROPANECARBONITRILE AND SUBSTITUTED PHENYLTHIO DERIVATIVES THEREOF AS CROP PROTECTANTS

[75] Inventor: Rajendra K. Singh, Maryland Heights, Mo.

[73] Assignee: Monsanto Company, St. Louis, Mo.

[21] Appl. No.: 650,148

[22] Filed: Sep. 13, 1984

Related U.S. Application Data

[63] Continuation-in-part of Ser. No. 440,770, Nov. 10, 1982, abandoned.

[51] Int. Cl.$^4$ ................... A01N 43/70; C07C 121/66
[52] U.S. Cl. ........................................... 71/93; 71/88; 71/98; 71/100; 549/442; 558/426
[58] Field of Search ........... 260/465 R, 465 G, 465 F, 260/465 K; 549/442; 71/88, 93, 98, 100

[56] References Cited

U.S. PATENT DOCUMENTS

| | | | |
|---|---|---|---|
| 3,156,725 | 11/1964 | Kaiser et al. | 260/570.5 |
| 3,221,018 | 11/1965 | Biel et al. | 260/295 |
| 3,282,979 | 11/1966 | Reifschneider et al. | 260/465 |
| 3,576,834 | 4/1971 | Buchanan | 260/453 |
| 3,910,957 | 10/1975 | Pfister et al. | 260/335 |
| 4,028,413 | 6/1977 | Magee | 260/566 |
| 4,096,144 | 6/1978 | Yamamoto et al. | 544/284 |

FOREIGN PATENT DOCUMENTS 810023  1/1981  South Africa .

OTHER PUBLICATIONS

Makosza et al., "Reactions of Organic Anions. XLII. Catalytic Alkylation of S-Phenylthioglycolonitrile in Aqueous Medium", *Tetrahedron Letters*, No. 23, pp. 2391–2394 (1972).

*Primary Examiner*—Dolph H. Torrence
*Attorney, Agent, or Firm*—J. Timothy Keane; Paul D. Matukaitis

[57] ABSTRACT

1-Phenylthio-1-cyclopropanecarbonitrile and substituted phenylthio derivatives thereof reduce herbicidal injury of certain food crops treated with a herbicide for control of weeds.

32 Claims, No Drawings

1-PHENYLTHIO-1-CYCLOPROPANECARBONITRILE AND SUBSTITUTED PHENYLTHIO DERIVATIVES THEREOF AS CROP PROTECTANTS

CROSS REFERENCE TO RELATED APPLICATION

This application is a continuation-in-part of co-pending U.S. application Ser. No. 440,770 filed Nov. 10, 1982, abandoned.

FIELD OF THE INVENTION

This invention relates to novel substituted phenylthio derivatives of 1-phenylthio-1-cyclopropanecarbonitrile. The invention also relates to the use of 1-phenylthio-1-cyclopropanecarbonitrile and substituted phenylthio derivatives thereof in compositions and methods for reducing injury to crop plants treated with herbicides.

BACKGROUND OF THE INVENTION

Many herbicides injure crop plants by slowing crop plant growth and development at herbicide application rates necessary to control weed growth. Accordingly, many herbicides cannot be used for controlling weeds in the presence of certain crops. Reduction of herbicidal injury to crops without an unacceptable corresponding reduction of herbicidal action on the weeds can be accomplished by use of crop protectants (also known as "herbicide antidotes" or "safeners"). A new class of crop protectants is provided by 1-phenylthio-1-cyclopropanecarbonitrile and substituted phenylthio derivatives thereof.

Preparation of 1-phenylthio-1-cyclopropanecarbonitrile, by reaction of α-phenylthioacetonitrile with ethylene dibromide, is described in a publication of Makosza et al [*Tetrahedron Letters*, No. 23, pp. 2391–2394 (1972)]. There is no suggestion that the cyclopropanecarbonitriles shown in the Makosza publication are useful as crop protectants.

DESCRIPTION OF THE INVENTION

Herbicidal injury to crop plants may be reduced by application to the crop plant locus of an effective amount of a safening agent having the structural formula:

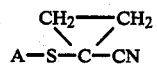

wherein A is selected from the group consisting of naphthalenyl, tetrahydronaphthalenyl, benzodioxol, and

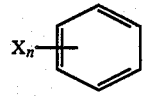

wherein X is independently selected from the group consisting of halogen, haloalkyl, alkyl, alkenyl, alkoxy, alkylthio, alkylcarbonyl, alkylalkenyl, and cycloalkyl; and n is 0 or a whole number from 1 through 5. Examples of the radical "naphthalenyl" are 1-naphthalenyl and 2-naphthalenyl. Examples of the radical "tetrahydronaphthalenyl" are 1-tetrahydronaphthalenyl and 2-tetrahydronaphthalenyl. Examples of the radical "benzodioxol" are 2,3-methylenedioxyphenyl and 3,4-methylenedioxyphenyl. The term "halogen", as used herein, includes chloro, bromo, fluoro and iodo radicals. The term "haloalkyl" means alkyl moieties wherein at least one hydrogen atom has been replaced by a halogen including, for example, chloromethyl, iodobutyl, dichloroethyl, dibromopropyl, trichloromethyl, trifluoromethyl, and the like. The term "alkyl" means straight and branched alkyl radicals including, for example, methyl, ethyl, n-propyl, isopropyl, n-butyl, sec-butyl, tert-butyl, n-pentyl, isopentyl, 1-methylethyl, 1,1-dimethylethyl, 1-methylpropyl, 2-methylpropyl, 1,1-dimethylpropyl, and the like. The term "alkenyl" means straight or branched chain radicals containing at least one carbon-carbon double bond including, for example, ethenyl, propenyl and the like. The term "alkoxy" means straight or branched chain alkoxy radicals including, for example, methoxy, ethoxy, n-propoxy, isopropoxy, n-butoxy, sec-butoxy, tert-butoxy, n-pentoxy, isopentoxy, and the like. The term "alkylthio" means straight or branched chain alkyl radicals containing at least one divalent sulfur atom including, for example, methylthio, ethylthio, propylthio, isopropylthio, butylthio, pentylthio, and the like. The terms "alkylcarbonyl" means straight or branched chain alkyl radicals containing at least one carbonyl group including, for example, acetyl, propionyl, pivaloyl, and the like. The term "alkylalkenyl" means straight or branched chain alkyl radicals containing at least one carbon-carbon double bond, including, for example, 1-propenyl, 2-methyl-1-propenyl, and the like. The term "cycloalkyl" means cyclic moieties composed of three or more alkylene groups including, for example, cyclopropyl, cyclobutyl, cyclopentyl, cyclohexyl, cycloheptyl, cyclooctyl, and the like.

Of the foregoing substituents, namely, haloalkyl, alkyl, alkenyl, alkoxy, alkythio, alkylcarbonyl, alkylalkenyl and cycloalkyl, those substituents having one to six carbon atoms are preferred.

Herbicides which may be used with benefit in combination with a safening agent of the described class include thiocarbamates, triazines and acetamides. Examples of thiocarbamates herbicides are cis-/trans-2,3-dichloroallyldiisopropylthiocarbamate (common name "diallate") and 2,3,3-trichloroallyldiisopropylthiocarbamate (common name "triallate"). An example of a triazine herbicide is 2-chloro-4-ethylamino-6-isopropylamino-1,3,5-triazine (common name "atrazine"). Examples of acetamide herbicides are 2-chloro-2',6'-diethyl-N-(methoxymethyl)acetanilide (common name "alachlor"); 2-chloro-N-isopropylacetanilide (common name "propachlor"); N-(ethoxymethyl)-N-(2-ethyl-6-methyl-1-cyclohexen-1-yl)-2-chloroacetamide; N-(ethoxymethyl)-N-(2,5-dimethyl-1-cyclopenten-1-yl)-2-chloroacetamide; 2-chloro-N-(2-methoxy-1-methylethyl)-6'-ethyl-o-acetotoluidide; 2-chloro-N-(ethoxymethyl)-6'-ethyl-o-acetotoluidide (common name "acetochlor"); ethyl ester of N-chloroacetyl-N-(2,6-diethylphenyl)glycine; 2-chloro-2',3'-dimethyl-N-(isopropyl)acetanilide; 2-chloro-2',-6'-diethyl-N-(pyrazolylmethyl)acetanilide; 2-chloro-6'-trifluoromethyl-N-(isopropoxymethyl)-acetanilide; 2-chloro-2'-methyl-6'-trifluoromethyl-N-(isopropoxymethyl)acetanilide; 2-chloro-2'-methyl-6'-trifluoromethyl-N-(ethoxymethyl)acetanilide; 2-chloro-2'-methyl-6'-methoxy-N-(isopropoxymethyl)acetanilide; 2-chloro-2'-methyl-6'-methoxy-N-(propoxymethyl)acetanilide; 2-chloro-2'- isobutoxy-6'-methyl-N-(propoxymethyl)acetanilide; 2-chloro-2'-isobutoxy-6'-ethyl-N-(ethoxymethyl)acetanilide; and 2-chloro-2'-methyl-6'-ethoxy-N-(propoxymethyl)acetanilide.

Many of the safener compounds of the invention are especially useful to reduce herbicidal injury to wheat plants and wheat seed caused by triallate herbicide.

The terms "safening agent", "safener", "antidote", "antagonistic agent", "crop protectant" and "crop protective" are equivalent terms denoting a compound capable of reducing the phytotoxicity of a herbicide to a plant. The terms "crop protectant" and "crop protective" are sometimes used to denote a herbicide-safener combination which provides protection from competitive weed growth by reducing herbicidal injury to valuable crop plant while at the same time suppressing weed growth.

The amount of safening agent employed in the methods and compositions of the invention will vary depending upon the particular herbicide with which the agent is employed, the rate of application of the herbicide, the particular food crop to be protected, and the manner of application to the plant locus. In each instance the amount of agent employed is a safening-effective amount, that is, the amount which reduces, or protects against, crop injury that otherwise would result from the presence of the herbicide. The amount of safening agent employed will be less than an amount that will substantially injure the crop plant.

By application to the "plant locus" is meant application to the plant growing medium, such as soil, as well as to the seeds, emerging seedlings, roots, stems, leaves, or other plant parts.

The safening agent can be applied to the crop plant locus in a mixture with the selected herbicide. For example, where the crop seed is first planted, a suitable mixture of safening agent and herbicide, whether in a homogenous liquid, emulsion, suspension or solid form, can be applied to the surface of, or incorporated in, the soil in which the seed has been planted. Or, the herbicide-safener mixture may be applied to the soil, and then the seed thereafter "drilled" into the soil below the soil layer containing the herbicide-safener mixture. The herbicide will reduce or eliminate the presence of undesirable weed and grass plants. Where the herbicide would by itself injure the crop seed, the presence of the safening agent will reduce or eliminate the injury to the crop seed caused by the herbicide. It is not essential that the application of herbicide and the safening agent to the plant locus be made using the selected herbicide and safening agent in the form of a mixture or composition. The herbicide and the safening agent may be applied to the plant locus in a sequential manner. For example, the safening agent may be first applied to the plant locus and thereafter the herbicide is applied. Or, the herbicide may be first applied to the plant locus and thereafter the safening agent is applied.

The application of the safening agent can be made directly to the seed before planting. In this practice, a quantity of crop seed is first coated with the safening agent. The coated seed is thereafter planted. Then, the herbicide is applied to soil in which the coated seed has been planted.

Several of the mentioned herbicides are known in the art. Propachlor and its herbicidal use are disclosed in U.S. Pat. No. 2,863,752 and U.S. Pat. Re. No. 26,961. U.S. Pat. No. 3,937,730 discloses and claims 2-chloro-N-(2-methoxy-1-methylethyl)-6'-ethyl-o-acetotoluidide.

The herbicidal use of N-(ethoxymethyl)-N-(2-ethyl-6-methyl-1-cyclohexen-1-yl)-2-chloroacetamide and of N-(ethoxymethyl)-N-2-(2,5-dimethyl-1-cyclopenten-1-yl)-2-chloroacetamide are disclosed in U.S. Pat. No. 4,351,667. Alachlor, butachlor and acetochlor and their herbicidal uses are disclosed in U.S. Pat. No. 3,442,945 and U.S. Pat. No. 3,547,620.

The novel compounds can be prepared by reacting an arylthioacetonitrile with 1,2-dihaloethane in the presence of a base catalyst as shown, for example, in the equation set forth above in Table 1. The selected arylthioacetonitrile and dihaloethane may be reacted directly together without the use of a solvent or may be reacted in an inert solvent at a temperature from about 0° C. to about 150° C., preferably from about 20° C. to about 80° C., and at a pressure from about 1 to about 10 atmospheres, preferably from about 1 to about 2 atmospheres. Normally, the reaction is conducted at atmospheric pressure, although the pressure can be lower or higher than atmospheric, if needed to control the reaction or maintain the reactants and products in the desired phase. Useful inert solvents include aliphatic and aromatic hydrocarbons, such as methylene chloride, and the like. The reaction may be carried out in the presence of a quaternary ammonium catalyst, such as tetraethyl ammonium chloride, triethylbenzyl ammonium chloride, and the like, in a amount from about 0.1 to about 5.0% by weight, based on the weight of the reactants. The molar ratio of acetonitrile to dihaloethane can vary from about 1:1.5 to about 1:3. An excess amount of dihaloethane is preferred to ensure complete reaction of the acetonitrile. Reaction times can vary from a few minutes to several days. Usually, reaction times of less than 24 hours are sufficient.

The following examples are presented for illustrative purposes only and are not intended as a restriction on the scope of the invention. All parts are by weight unless otherwise indicated. The 1-phenylthio-1-cyclopropanecarbonitriles of the present invention can be prepared according to the general procedure described in Example 1. Table 1 set forth physical and chemical data for specific compounds prepared in accordance with the general procedures of Example 1.

EXAMPLE 1

The 1-phenylthio-1-cyclopropanecarbonitriles are prepared by cyclopropanation of α-arylthioacetonitriles. An α-arylthioacetonitrile was prepared by reacting an aryl thiol with a haloacetonitrile in a known manner. Carbonitrile compounds listed in Table 1 were prepared, typically, by dissolving the selected aryl thiol (about 0.4 mole) in tetrahydrofuran (about 400 ml) and triethylamine (about 0.5 mole) so as to form a mixture. Then, chloroacetonitrile (about 0.44 mole) was slowly added to the mixture. The resulting reaction mixture was stirred overnight. The mixture was then diluted with about 400 ml of diethyl ether. Triethylammonium hydrochloride precipitated from the mixture and was removed by filtration. The precipitate was then washed with additional ether. The combined filtrate was concentrated by evaporating the ether. The α-arylthioacetonitrile product was purified by a distillation procedure in the case of a normally liquid product, or by crystallization from 95% ethanol in the case of a normally solid product. Then, the appropriately selected arylthioacetonitrile (about 0.1 mole), 1,2-dibromoethane (about 0.3 mole) and triethylbenzyl ammonium chloride (TEBA) (about 1.0 gm), as catalyst, were brought together to form a mixture in a reaction vessel equipped with stirring means. To this stirred mixture, about 50 ml of 50% sodium hydroxide solution was added. Waterbath cooling was applied in cases where the reaction temperature exceeded 50° C. Stirring was continued for at least four hours. In some cases stirring was continued overnight when convenient. The reaction mixture was diluted with 100 ml of water and extracted four times with 100 ml of diethyl ether. The resulting organic layer containing the carbonitrile was washed with water, brine and then dried over magnesium sulfate. The solvent was removed by evaporation and the nitrile product was either distilled or crystalized to purify the product, as appropriate.

TABLE 1

$$X_n-\text{C}_6\text{H}_4-\text{SCH}_2\text{CN} + \text{BrCH}_2\text{CH}_2\text{Br} \xrightarrow[\text{NaOH}]{\text{TEBA Cat.}} X_n-\text{C}_6\text{H}_4-\text{S}-\text{C}(\text{CH}_2\text{CH}_2)-\text{CN} + \text{NaBr}$$

| Compound No. | X | % Yield | 1. MP/or 2. BP° C. | % C Calc'd | % C Found | % H Calc'd | % H Found | % Hal Calc'd | % Hal Found | % N Calc'd | % N Found | % S Calc'd | % S Found |
|---|---|---|---|---|---|---|---|---|---|---|---|---|---|
| 1 | 3-CF$_3$ | 82 | 107(2) | 54.3 | 54.1 | 3.3 | 3.4 | 23.4 | — | 5.8 | 5.7 | 13.2 | 13.1 |
| 2 | 4-chloro | 87 | 42–46(1) | 57.3 | 57.2 | 3.9 | 3.9 | 16.9 | 16.9 | 6.7 | 6.7 | 15.3 | — |
| 3 | 3,4-dichloro | 79 | 61(1) | 49.2 | 49.3 | 2.9 | 2.9 | 29.0 | 28.9 | 5.7 | 5.7 | — | — |
| 4 | 2,6-dichloro | 89 | 57(1) | 44.1 | 44.0 | 2.3 | 2.4 | 32.5 | 32.4 | 6.4 | 6.4 | — | — |
| 5 | 2,5-dichloro | 69 | 119(1) | 49.2 | 49.1 | 2.9 | 3.0 | 29.0 | 28.9 | 5.7 | 5.7 | — | — |
| 6 | none | 89 | 116(2) | 65.8 | 66.0 | 5.4 | 5.1 | — | — | 7.7 | 7.4 | 18.3 | — |
| 7 | 2,4,5-trichloro | 69 | 123(1) | 43.1 | 43.0 | 2.2 | 2.2 | 38.2 | 38.1 | 5.0 | 5.0 | 11.5 | — |
| 8 | 2-chloro | 40 | 73(1) | 57.3 | 57.1 | 3.9 | 3.9 | 16.9 | 16.8 | 6.7 | 6.6 | 15.3 | 15.3 |
| 9 | 3-chloro | 71 | 139–42(2) | 57.3 | 57.2 | 3.9 | 3.9 | 16.9 | 16.8 | 6.7 | 6.6 | 15.3 | 15.3 |
| 10 | 4-fluoro | 95 | 120(2) | 62.2 | 62.1 | 4.2 | 4.2 | 9.8 | — | 7.3 | 7.2 | 16.6 | 16.6 |
| 11 | 2-bromo | 97 | 69–72(1) | 47.3 | 47.4 | 3.2 | 3.2 | 31.4 | 31.2 | 5.5 | 5.5 | — | — |
| 12 | 4-methoxy | 81 | 124(2) | 64.4 | 62.7 | 5.6 | 5.3 | — | — | 6.8 | 6.6 | 15.6 | 16.2 |
| 13 | 4-t-butyl | 87 | 131(2) | 72.7 | 72.4 | 7.4 | 7.5 | — | — | 6.1 | 6.0 | 13.9 | — |
| 14 | 4-methyl | 83 | 103–8(2) | 69.8 | 69.7 | 5.9 | 5.9 | — | — | 7.4 | 7.4 | 16.9 | — |
| 15 | 2-isopropyl | 94 | 125(2) | 71.8 | 70.8 | 6.9 | 7.1 | — | — | 6.4 | 6.1 | 14.8 | — |
| 16 | 2-methyl | 63 | 117(2) | 69.8 | 68.9 | 5.9 | 5.8 | — | — | 7.4 | 7.3 | 16.9 | — |
| 17 | 4-bromo | 63 | 93(1) | 42.1 | 42.1 | 2.6 | 2.7 | 35.0 | 35.0 | 6.1 | 6.1 | 12.6 | — |
| 18 | 2-ethyl | 92 | 126(2) | 70.9 | 70.0 | 6.5 | 6.5 | — | — | 6.9 | 6.8 | 15.8 | — |
| 19 | 2,3-dimethyl | 30 | 123–36(2) | 70.9 | 69.9 | 6.5 | 6.5 | — | — | 6.9 | 6.2 | — | — |
| 20 | 3,4-dimethyl | 63 | 120–27(2) | 70.9 | 67.0 | 6.5 | 6.5 | — | — | 6.9 | 6.2 | — | — |
| 21 | 3,5-di-CF$_3$ | 81 | 99(2) | 46.3 | 46.2 | 2.3 | 2.3 | — | — | 4.5 | 4.4 | 10.3 | 10.3 |
| 22 | 2,4-di-CF$_3$ | 84 | 104(2) | 46.3 | 46.4 | 2.3 | 2.3 | — | — | 4.5 | 4.5 | 10.3 | 10.4 |
| 23 | 3,4-methylenedioxy | 12 | 55–57(1) | 60.3 | 59.9 | 4.1 | 4.3 | — | — | 6.4 | 6.2 | 14.6 | 14.4 |
| 24 | 3-bromo | 74 | 45(1) | 47.2 | 47.3 | 3.1 | 3.1 | — | — | 5.5 | 5.4 | 12.6 | 12.6 |
| 25 | 2,6-di-CH$_3$ | 13 | 91–96(1) | 70.9 | 70.7 | 6.5 | 6.5 | — | — | 6.9 | 6.9 | 15.8 | 15.9 |
| 26 | 2,4-di-Cl—3,5-di-CH$_3$ | 17 | 130–2(1) | 53.0 | 52.9 | 4.1 | 4.1 | 26.1 | 26.1 | 5.2 | 5.1 | 11.8 | 11.9 |
| 27 | 4-SCH$_3$ | 92 | 37.5–40(1) | 59.7 | 59.6 | 5.0 | 5.0 | — | — | 6.3 | 6.2 | 29.0 | 28.9 |
| 28 | 2,4-di-Cl | 64 | 69–71(1) | 49.2 | 49.1 | 2.9 | 2.9 | 29.0 | 29.1 | 5.7 | 5.7 | 13.1 | 13.2 |
| 29 | 2,4-di-CH$_3$ | 57 | 106–112(2) | 70.9 | 70.7 | 6.5 | 6.5 | — | — | 6.9 | 6.8 | 15.8 | 15.7 |
| 30 | 2-fluoro | 83 | 100–104(2) | 62.2 | 62.1 | 4.2 | 4.2 | — | — | 7.3 | 7.2 | 16.6 | 16.7 |
| 31 | 3-methyl | 80 | 117(1) | 67.2 | 67.2 | 6.0 | 5.7 | — | — | 7.1 | 6.5 | — | — |
| 32 | 4-isopropyl | 90 | 156–60(2) | 71.8 | 71.8 | 6.9 | 7.0 | — | — | 6.4 | 6.4 | — | — |
| 33 | 2,6-diethyl | 56 | 143–46(2) | 72.7 | 72.7 | 7.4 | 7.4 | — | — | 6.0 | 6.0 | — | — |
| 34 | 2,5-dimethyl | 66 | 57–60(1) | 70.9 | 70.7 | 6.4 | 6.5 | — | — | 6.9 | 6.8 | 15.8 | 15.8 |
| 35 | 4-n-butyl | 72 | 144–48(2) | 72.7 | 72.5 | 7.4 | 7.4 | — | — | 6.0 | 6.0 | 13.9 | 13.9 |
| 36 | 2-methoxy | 53 | 108–114(2) | 64.4 | 64.2 | 5.4 | 5.4 | — | — | 6.8 | 6.8 | 15.6 | 15.7 |
| 37 | 3,5-dimethyl | 30 | 108–15(2) | 70.9 | 70.9 | 6.5 | 6.5 | — | — | 6.9 | 6.9 | 15.8 | 15.7 |
| 38 | 2-s-butyl | 64 | 112–116(2) | 72.7 | 72.5 | 7.4 | 7.5 | — | — | 6.1 | 6.0 | 13.9 | 13.9 |
| 39 | 2,4,6-tri-(isopropyl) | 11 | 73–74.5(1) | 75.7 | 75.6 | 9.0 | 9.1 | — | — | 4.7 | 4.6 | 10.6 | 10.7 |
| 40 | 3,4-benzo | 36 | 60–66(1) | 74.6 | 74.0 | 4.9 | 4.9 | — | — | 6.2 | 6.1 | 14.2 | 14.1 |
| 41 | dimethyl isomer mixture | 54 | 126–130(2) | 70.9 | 71.0 | 6.5 | 6.5 | — | — | 6.9 | 6.9 | — | — |
| 42 | 3,5-dichloro | 34 | 66(1) | 49.2 | 49.3 | 2.9 | 2.9 | 29.0 | 29.1 | 5.7 | 5.7 | — | — |
| 43 | 3-methoxy | 77 | 124–134(2) | 64.4 | 64.5 | 5.4 | 5.4 | — | — | 6.8 | 6.8 | 15.6 | 15.7 |
| 44 | 2,4,5-trimethyl | 74 | 84–87(1) | 71.8 | 71.8 | 7.0 | 7.0 | — | — | 6.4 | 6.4 | 14.7 | 14.7 |
| 45 | 2-t-butyl | 73 | 118–120(2) | 72.7 | 72.5 | 7.4 | 7.5 | — | — | 6.1 | 6.0 | 13.9 | 13.9 |
| 46 | 2,4,6-trimethyl | 24 | 64–68(1) | 71.8 | 71.7 | 7.0 | 7.0 | — | — | 6.4 | 6.4 | 14.8 | 14.8 |
| 47 | 2,3-dichloro | 86 | 114–16(1) | 49.2 | 49.2 | 2.9 | 2.9 | 29.0 | 29.0 | 5.7 | 5.7 | 13.1 | 13.1 |
| 48 | 4-bromo, 3-methyl | 84 | 66–68(1) | 49.3 | 49.4 | 3.8 | 3.8 | 29.8 | 29.8 | 5.2 | 5.2 | 12.0 | 11.9 |
| 49 | 2,4-di(isopropyl) | 75 | 125–130(2) | 74.0 | 74.0 | 8.2 | 8.2 | — | — | 5.4 | 5.4 | 12.4 | 12.4 |
| 50 | 3-chloro, 4-fluoro | 82 | 103–110(2) | 52.8 | 52.8 | 3.1 | 3.2 | 15.6 | 15.6 | 6.2 | 6.1 | 14.1 | 14.0 |
| 51 | 3,4-tetramethylene | 98 | 127–130(2) | 70.9 | 70.8 | 6.5 | 6.5 | — | — | 6.9 | 6.8 | 15.8 | 15.8 |

TABLE 1-continued

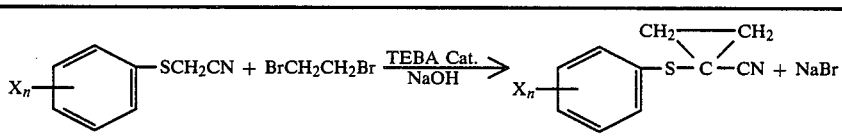

| Compound No. | X | % Yield | 1. MP/or 2. BP° C. | % C Calc'd | % C Found | % H Calc'd | % H Found | % Hal Calc'd | % Hal Found | % N Calc'd | % N Found | % S Calc'd | % S Found |
|---|---|---|---|---|---|---|---|---|---|---|---|---|---|
| 52 | 4-chloro,2,5-dimethyl | 67 | 103–105(1) | 60.6 | 60.5 | 5.1 | 5.1 | 14.9 | 15.0 | 5.9 | 5.8 | 13.5 | 13.4 |
| 53 | 2-pivaloyl | 16 | 73–77(1) | 69.5 | 69.2 | 6.6 | 6.7 | — | — | 5.4 | 5.3 | 12.4 | 12.3 |
| 54 | 2,6-difluoro | 34 | 40–41(1) | 56.9 | 56.7 | 3.3 | 3.4 | — | — | 6.6 | 6.6 | 15.2 | 15.3 |
| 55 | 4-chloro, 3-CF₃ | 77 | 118–125(2) | 47.6 | 47.7 | 2.5 | 2.6 | 12.8 | 12.7 | 5.0 | 5.0 | 11.6 | 11.6 |
| 56 | 3,4-dimethoxy | 52 | 66–68(1) 147–150(2) | 60.3 | 60.2 | 5.7 | 5.7 | — | — | 5.9 | 5.8 | 13.4 | 13.3 |
| 57 | 2-(1-methylbutyl) | 65 | 113–116(2) | 73.4 | 73.3 | 7.8 | 7.8 | — | — | 5.7 | 5.7 | 13.1 | 13.1 |
| 58 | 2-isobutyl | 79 | 109–112(2) | 72.7 | 72.6 | 7.4 | 7.5 | — | — | 6.1 | 6.0 | 13.9 | 13.8 |
| 59 | 4-t-amyl | 83 | 124–135(2) | 73.4 | 73.4 | 7.8 | 7.8 | — | — | 5.7 | 5.7 | 13.1 | 13.1 |
| 60 | 2-t-butyl, 4-methyl | 83 | 135–42(2) | 73.4 | 73.2 | 7.8 | 7.9 | — | — | 5.7 | 5.6 | 13.1 | 13.0 |
| 61 | 3-t-butyl | 77 | 129–134(2) | 72.7 | 72.7 | 7.4 | 7.4 | — | — | 6.1 | 6.0 | 13.9 | 13.8 |
| 62 | 4-chloro, 2-methyl | 63 | 54–56(1) | 59.1 | 59.0 | 4.5 | 4.6 | 15.9 | 15.8 | 6.3 | 6.2 | 14.3 | 14.3 |
| 63 | 2-(2-methyl-1-propenyl) | 33 | 108–111(2) | 73.3 | 73.2 | 6.6 | 6.6 | — | — | 6.1 | 6.1 | 14.0 | 14.0 |
| 64 | 4-cyclohexyl | 68 | 185–190(2) | 74.7 | 74.6 | 7.4 | 7.5 | — | — | 5.4 | 5.4 | 12.5 | 12.5 |

The compounds prepared are identified as follows:

| Compound No. | Name |
|---|---|
| 1 | 1-([3-trifluoromethyl)phenyl]thio)-1-cyclopropanecarbonitrile |
| 2 | 1-[(4-chlorophenyl)thio]-1-cyclopropanecarbonitrile |
| 3 | 1-[(3,4-dichlorophenyl)thio]-1-cyclopropanecarbonitrile |
| 4 | 1-[(2,6-dichlorophenyl)thio]-1-cyclopropanecarbonitrile |
| 5 | 1-[(2,5-dichlorophenyl)thio]-1-cyclopropanecarbonitrile |
| 6 | 1-(phenylthio)-1-cyclopropanecarbonitrile.0.4 H₂O |
| 7 | 1-[(2,4,5-trichlorophenyl)thio]-1-cyclopropanecarbonitrile |
| 8 | 1-[(2-chlorophenyl)thio]-1-cyclopropanecarbonitrile |
| 9 | 1-[(3-chlorophenyl)thio]-1-cyclopropanecarbonitrile |
| 10 | 1-[(4-fluorophenyl)thio]-1-cyclopropanecarbonitrile |
| 11 | 1-[(2-bromophenyl)thio]-1-cyclopropanecarbonitrile |
| 12 | 1-[(4-methoxyphenyl)thio]-1-cyclopropanecarbonitrile |
| 13 | 1-([4-(1,1-dimethylethyl)phenyl]thio)-1-cyclopropanecarbonitrile |
| 14 | 1-[(4-methylphenyl)thio]-1-cyclopropanecarbonitrile |
| 15 | 1-([2-(1-methylethyl)phenyl]thio-1-cyclopropanecarbonitrile |
| 16 | 1-[(2-methylphenyl)thio]-1-cyclopropanecarbonitrile |
| 17 | 1-[(4-bromophenyl)thio]-1-cyclopropanecarbonitrile |
| 18 | 1-[(2-ethylphenyl)thio]-1-cyclopropanecarbonitrile |
| 19 | 1-[(2,3-dimethylphenyl)thio]-1-cyclopropanecarbonitrile |
| 20 | 1-[3,4-diemthylphenyl)thio]-1-cyclopropanecarbonitrile |
| 21 | 1-([3,5-bis(trifluoromethyl)phenyl]thio)-1-cyclopropanecarbonitrile |
| 22 | 1-([2,4-bis(trifluoromethyl)phenyl]thio)-1-cyclopropanecarbonitrile |
| 23 | 1-[(1,3-benzodioxol-5-yl)thio]-1-cyclopropanecarbonitrile |
| 24 | 1-[(3-bromophenyl)thio]-1-cyclopropanecarbonitrile |
| 25 | 1-[(2,6-dimethylphenyl)thio]-1-cyclopropanecarbonitrile |
| 26 | 1-[(2,4-dichloro-3,5-dimethylphenyl)thio]-1-cyclopropanecarbonitrile |
| 27 | 1-([4-(methylthio)phenyl]thio)-1-cyclopropanecarbonitrile |
| 28 | 1-[(2,4-dichlorophenyl)thio]-1-cyclopropanecarbonitrile |
| 29 | 1-[(2,4-dimethylphenyl)thio]-1-cyclopropanecarbonitrile |
| 30 | 1-[(2-fluorophenyl)thio]-1-cyclopropanecarbonitrile |
| 31 | 1-[(3-methylphenyl)thio]-1-cyclopropanecarbonitrile |
| 32 | 1-([4-(1-methylethyl)phenyl]thio)-1-cyclopropanecarbonitrile |
| 33 | 1-[(2,6-diethylphenyl)thio]-1-cyclopropanecarbonitrile |
| 34 | 1-[(2,5-dimethylphenyl)thio]-1-cyclopropanecarbonitrile |
| 35 | 1-[(4-butylphenyl)thio]-1-cyclopropanecarbonitrile |
| 36 | 1-[(2-methoxyphenyl)thio]-1-cyclopropanecarbonitrile |
| 37 | 1-[(3,5-dimethylphenyl)thio]-1-cyclopropanecarbonitrile |
| 38 | 1-([2-(1-methylpropyl)phenyl]thio)-1-cyclopropanecarbonitrile |
| 39 | 1-([2,4,6-tris(1-methylethyl)phenyl]thio)-1-cyclopropanecarbonitrile |
| 40 | 1-[(2-naphthalenyl)thio]-1-cyclopropanecarbonitrile.0.1 H₂O |
| 41 | 1-[(dimethylphenyl)thio]-1-cyclopropanecarbonitrile isomer mixture |
| 42 | 1-[(3,5-dichlorophenyl)thio]-1-cyclopropanecarbonitrile |
| 43 | 1-[(3-methoxyphenyl)thio]-1-cyclopropanecarbonitrile |

| Compound No. | Name |
| --- | --- |
| 44 | 1-[(2,4,5-trimethylphenyl)thio]-1-cyclopropanecarbonitrile |
| 45 | 1-([2-(1,1-dimethylethyl)phenyl]thio)-1-cyclopropanecarbonitrile |
| 46 | 1-[(2,4,6-trimethylphenyl)thio]-1-cyclopropanecarbonitrile |
| 47 | 1-[(2,3-dichlorophenyl)thio]-1-cyclopropanecarbonitrile |
| 48 | 1-[(4-bromo-3-methylphenyl)thio]-1-cyclopropanecarbonitrile |
| 49 | 1-([2,4-bis(1-methylethyl)phenyl]thio)-1-cyclopropanecarbonitrile |
| 50 | 1-[(3-chloro-4-fluorophenyl)thio]-1-cyclopropanecarbonitrile |
| 51 | 1-[ 3,4(tetramethylene)phenylthio]-1-cyclopropanecarbonitrile or 1-[(5,6,7,8-tetrahydro-2-naphthalenyl)thio]-1-cyclopropanecarbonitrile |
| 52 | 1-[(4-chloro-2,5-dimethylphenyl)thio]-1-cyclopropanecarbonitrile |
| 53 | 1-([2-(2,2-dimethyl-1-oxopropyl)phenyl]thio)-1-cyclopropanecarbonitrile |
| 54 | 2-[(2,6-difluorophenyl)thio]-1-cyclopropanecarbonitrile |
| 55 | 1-([4-chloro-3-(trifluoromethyl)phenyl]thio)-1-cyclopropanecarbonitrile |
| 56 | 1-[(3,4-dimethoxyphenyl)thio]-1-cyclopropanecarbonitrile 0.2 H$_2$O |
| 57 | 1-([2-(1-methylbutyl)phenyl]thio)-1-cyclopropanecarbonitrile |
| 58 | 1-([2-(2-methylpropyl)phenyl]thio)-1-cyclopropanecarbonitrile |
| 59 | 1-([4-(1,1-dimethylpropyl)phenyl]thio)-1-cyclopropanecarbonitrile |
| 60 | 1-([2-(1,1-dimethylethyl)-4-methylphenyl]thio)-1-cyclopropanecarbonitrile |
| 61 | 1-([3-(1,1-dimethylethyl)phenyl]thio)-1-cyclopropanecarbonitrile |
| 62 | 1-[(4-chloro-2-methylphenyl)thio]-1-cyclopropanecarbonitrile |
| 63 | 1-([2-(2-methyl-1-propenyl)phenyl]thio)-1-cyclopropanecarbonitrile and 1-([2-(2-methyl-2-propenyl)phenyl]thio)-1-cyclopropanecarbonitrile isomer mixture |
| 64 | 1-[(4-cyclohexylphenyl)thio]-1-cyclopropanecarbonitrile |

EXAMPLE 2

The following procedure shows interaction between herbicide and safener when both are incorporated in a soil cover layer before emergence of the crop species:

A fumigated silt loam top soil was placed in a first container and compacted to a depth of about 1.3 cm from the top of the first container. A predetermined amount of seed of each of the crop species to be tested was placed on top of the soil in the first container. A quantity of soil, sufficient to substantially fill the first container, was measured and placed in a second container. A measured quantity of herbicide dispersed or dissolved in a suitable carrier was applied to the soil in the second container. A measured quantity of safening agent dispersed or dissolved in a suitable carrier was thereafter sprayed on the soil already treated with the herbicide. The soil in the second container treated with the safening agent and herbicide was thoroughly mixed. This mixing is sometimes referred to as incorporation of the herbicide and safening agent into the soil. The mixing or incorporation provides a substantially uniform distribution of the safening agent in the soil. The seed in the first container of soil was covered with the soil treated with the safening agent and herbicide and the containers were leveled. For each test series, a seeded container was prepared having soil containing no herbicide and no safening agent as a blank control. Also, a seeded container was prepared having soil treated with herbicide alone. The containers were then placed on a sand bench in a greenhouse and watered from below as needed. The plants were observed at the end of approximately 21 days and the results in terms of percent inhibition of growth were recorded.

The degree of injury to the crop species was determined firstly by making a visual comparison of the crop plant in the herbicide-safener treated container against the crop plant in the blank control container and then assigning a number to the visual comparison expressed as "Percent Plant Inhibition". Secondly, a visual comparison was made between the crop plant in the herbicide-alone-treated container and the crop plant in the blank control container. Then a number is assigned to the visual comparison indicating the percent injury or inhibition to the herbicide-treated-alone crop plant. Table I reports the "Percent Plant Inhibition" data for the herbicide-with-safener crop plant (Column "W") and for the herbicide-without-safener crop plant (column "WO"). The degree of safening effect provided by a safener compound is proportional to the magnitude that a plant inhibition number in column "WO" exceeds the corresponding number in column "W". Herbicides tested are identified by code number as shown in the "Herbicide Key", below. Herbicide application rates are given in kilograms per hectare (kg/ha). For all safener compounds listed in Table 2, the safener application rate was 9.0 kg/ha.

| No. | Herbicide Key: Name |
| --- | --- |
| 1 | 2,3,3-trichloroallyldiisopropylthiocarbamate (triallate) |
| 2 | 2-chloro-4-ethylamino-6-isopropylamino-1,3,5-triazine (atrazine) |
| 3 | 2-chloro-2',6'diethyl-N—(methoxymethyl)acetanilide (alachlor) |
| 4 | 2-chloro-2'-methyl-6'-methoxy-N—(isopropoxymethyl)-acetanilide |

TABLE 2

| Herbicide | | Compound | % Plant Inhibition | | | | | | | | |
| --- | --- | --- | --- | --- | --- | --- | --- | --- | --- | --- | --- |
| | | | Sorghum | | Wheat | | Rice | | Soybean | | Corn |
| No. | Rate | No. | W | Wo | W | Wo | W | Wo | W | Wo | W | Wo |
| 1 | 0.56 | 3 | | | 100 | 100 | | | | | | |
| 1 | 0.56 | 4 | | | 90 | 100 | | | | | | |
| 1 | 0.56 | 5 | | | 100 | 100 | | | | | | |
| 1 | 0.56 | 6 | | | 70 | 100 | | | | | | |
| 1 | 0.56 | 7 | | | 80 | 90 | | | | | | |

TABLE 2-continued

| Herbicide | | Compound | Sorghum | | Wheat | | Rice | | Soybean | | Corn | |
|---|---|---|---|---|---|---|---|---|---|---|---|---|
| No. | Rate | No. | W | Wo | W | Wo | W | Wo | W | Wo | W | Wo |
| 1 | 0.56 | 8 | | | 90 | 100 | | | | | | |
| 1 | 0.56 | 9 | | | 75 | 100 | | | | | | |
| 1 | 0.56 | 10 | | | 90 | 100 | | | | | | |
| 1 | 0.56 | 11 | | | 85 | 90 | | | | | | |
| 1 | 0.56 | 12 | | | 50 | 50 | | | | | | |
| 1 | 0.56 | 13 | | | 20 | 85 | | | | | | |
| 1 | 0.22 | 13 | | | 20 | 95 | | | | | | |
| 1 | 0.56 | 13 | | | 30 | 99 | | | | | | |
| 1 | 2.2 | 13 | | | 99 | 100 | | | | | | |
| 1 | 1.2 | 13 | | | 95 | 99 | | | | | | |
| 1 | none | 13 | | | 0 | 0 | | | | | | |
| 1 | 0.56 | 14 | | | 85 | 85 | | | | | | |
| 1 | 0.56 | 15 | | | 40 | 90 | | | | | | |
| 1 | 0.56 | 16 | | | 70 | 90 | | | | | | |
| 1 | 0.56 | 17 | | | 70 | 90 | | | | | | |
| 1 | 0.56 | 18 | | | 60 | 90 | | | | | | |
| 1 | 0.56 | 19 | | | 90 | 85 | | | | | | |
| 1 | 0.56 | 20 | | | 90 | 85 | | | | | | |
| 1 | 0.56 | 21 | | | — | — | | | | | 80 | 80 |
| 1 | 0.56 | 22 | | | 100 | 90 | | | | | | |
| 3 | 0.56 | 1 | | | 80 | 90 | | | | | | |
| 3 | 2.2 | 2 | 90 | 80 | 65 | 75 | | | | | | |
| 3 | 2.2 | 3 | 75 | 85 | 70 | 70 | | | | | | |
| 3 | 2.2 | 4 | 40 | 70 | 70 | 75 | | | | | | |
| 3 | 2.2 | 5 | 85 | 70 | 75 | 75 | | | | | | |
| 3 | 2.2 | 6 | 95 | 70 | 50 | 75 | | | | | | |
| 3 | 2.2 | 7 | | | 80 | 90 | | | 90 | 85 | | |
| 3 | 2.2 | 8 | 90 | 95 | | | | | | | | |
| 3 | 2.2 | 9 | 90 | 95 | 55 | 80 | | | | | | |
| 3 | 2.2 | 10 | 95 | 95 | 55 | 80 | | | | | | |
| 3 | 2.2 | 11 | 50 | 75 | 40 | 80 | | | | | | |
| 3 | 2.2 | 12 | 80 | 75 | 50 | 80 | | | | | | |
| 3 | 2.2 | 13 | 85 | 80 | 70 | 80 | | | | | | |
| 3 | 2.2 | 14 | 90 | 80 | 55 | 80 | | | | | | |
| 3 | 2.2 | 15 | 80 | 85 | 90 | 90 | | | | | | |
| 3 | 2.2 | 16 | 65 | 75 | 15 | 80 | | | | | | |
| 3 | 0.56 | 16 | 60 | 45 | 0 | 40 | | | | | | |
| 3 | none | 16 | 0 | | 0 | | | | | | | |
| 3 | 4.5 | 16 | 80 | 90 | 60 | 80 | | | | | | |
| 3 | 2.2 | 16 | 85 | 75 | 30 | 80 | | | | | | |
| 3 | 2.2 | 17 | 90 | 85 | 95 | 90 | | | | | | |
| 3 | 2.2 | 18 | 80 | 90 | 85 | 95 | | | | | | |
| 3 | 2.5 | 19 | 80 | 95 | 95 | 85 | | | | | | |
| 3 | 2.5 | 20 | 65 | 95 | 45 | 85 | | | | | | |
| 3 | 2.2 | 21 | 90 | 90 | 80 | 80 | | | | | | |
| 3 | 2.2 | 22 | 95 | 95 | 80 | 45 | | | | | | |
| 2 | 4.5 | 1 | | | | | 45 | 80 | 35 | 80 | | |
| 2 | 1.1 | 1 | | | | | 0 | 15 | 0 | 10 | | |
| 2 | 2.2 | 1 | | | | | 10 | 40 | 0 | 20 | | |
| 2 | 4.5 | 1 | | | | | 75 | 80 | 30 | 50 | | |
| 2 | 6.7 | 1 | | | | | 70 | 95 | 90 | 85 | | |
| 2 | none | 1 | | | | | 0 | | 0 | | | |
| 2 | 0.56 | 2 | | | 70 | 90 | | | | | | |
| 2 | 4.5 | 2 | | | | | 95 | 80 | 100 | 80 | | |
| 2 | 4.5 | 3 | | | | | 60 | 40 | 70 | 60 | | |
| 2 | 4.5 | 4 | | | | | 75 | 70 | 85 | 75 | | |
| 2 | 4.5 | 5 | | | | | 60 | 75 | 70 | 75 | | |
| 2 | 4.5 | 6 | | | | | 60 | 70 | 80 | 75 | | |
| 2 | 4.5 | 7 | | | | | 95 | 75 | 95 | 80 | | |
| 2 | 4.5 | 8 | | | | | 95 | 90 | 90 | 90 | | |
| 2 | 4.5 | 9 | | | | | 85 | 90 | 95 | 90 | | |
| 2 | 4.5 | 10 | | | | | 85 | 90 | 80 | 90 | | |
| 2 | 4.5 | 11 | | | | | 85 | 80 | 80 | 90 | | |
| 2 | 4.5 | 12 | | | | | 90 | 80 | 90 | 90 | | |
| 2 | 4.5 | 13 | | | | | 90 | 85 | 90 | 80 | | |
| 2 | 4.5 | 14 | | | | | 65 | 85 | 80 | 80 | | |
| 2 | 4.5 | 15 | | | | | 95 | 90 | 80 | 85 | | |
| 2 | 4.5 | 16 | | | | | 70 | 80 | 90 | 90 | | |
| 2 | 4.5 | 17 | | | | | 90 | 90 | 90 | 85 | | |
| 2 | 4.5 | 18 | | | | | 95 | 95 | | | 90 | 90 |
| 2 | 4.5 | 19 | | | | | 95 | 85 | 90 | 95 | | |
| 2 | 4.5 | 20 | | | | | 90 | 85 | 95 | 95 | | |
| 2 | 4.5 | 21 | | | 90 | 95 | 95 | 85 | 95 | 85 | | |
| 2 | 4.5 | 22 | | | | | 90 | 90 | 100 | 90 | | |
| 4 | 2.2 | 1 | | | | | | | | | 95 | 80 |
| 4 | 2.2 | 2 | | | | | | | | | 95 | 80 |
| 4 | 2.2 | 3 | | | | | | | | | 50 | 70 |
| 4 | 2.2 | 4 | | | | | | | | | 50 | 70 |

TABLE 2-continued

| Herbicide | | Compound | Sorghum | | Wheat | | Rice | | Soybean | | Corn | |
|---|---|---|---|---|---|---|---|---|---|---|---|---|
| No. | Rate | No. | W | Wo | W | Wo | W | Wo | W | Wo | W | Wo |
| 4 | 2.2 | 5 | | | | | | | | | 70 | 75 |
| 4 | 2.2 | 6 | | | | | | | | | 30 | 75 |
| 4 | 1.1 | 6 | | | | | | | | | 20 | 50 |
| 4 | 0.56 | 6 | | | | | | | | | 50 | 75 |
| 4 | 0.28 | 6 | | | | | | | | | 0 | 25 |
| 4 | 2.2 | 7 | | | | | | | | | 90 | 90 |
| 4 | 2.2 | 8 | | | | | | | | | 80 | 75 |
| 4 | 2.2 | 9 | | | | | | | | | 35 | 75 |
| 4 | 1.1 | 9 | | | | | | | | | 80 | 99 |
| 4 | 0.56 | 9 | | | | | | | | | 60 | 95 |
| 4 | 0.28 | 9 | | | | | | | | | 100 | 85 |
| 4 | none | 9 | | | | | | | | | | |
| 4 | 2.2 | 11 | | | | | | | | | 85 | 85 |
| 4 | 2.2 | 12 | | | | | | | | | 95 | 85 |
| 4 | 2.2 | 13 | | | | | | | | | 95 | 90 |
| 4 | 2.2 | 14 | | | | | | | | | 95 | 90 |
| 4 | 2.2 | 15 | | | | | | | | | 80 | 90 |
| 4 | 2.2 | 16 | | | | | | | | | | |
| 4 | 2.2 | 17 | | | | | | | | | 90 | 90 |
| 4 | 2.2 | 18 | | | | | | | | | 80 | 90 |
| 4 | 2.2 | 19 | | | | | | | | | 80 | 90 |
| 4 | 2.2 | 20 | | | | | | | | | 85 | 90 |
| 4 | 2.2 | 21 | | | | | | | | | | |
| 4 | 2.2 | 22 | | | | | | | | | 75 | 80 |
| 1 | 0.56 | 23 | | | 80 | 95 | | | | | | |
| 1 | 0.56 | 24 | | | 25 | 80 | | | | | | |
| 1 | 0.56 | 25 | | | 65 | 100 | | | | | | |
| 1 | 0.56 | 26 | | | 90 | 95 | | | | | | |
| 1 | 0.56 | 27 | | | 50 | 75 | | | | | | |
| 1 | 0.56 | 28 | | | 75 | 75 | | | | | | |
| 1 | 0.14 | 32 | | | | | | | | | | |
| 2 | 4.48 | 23 | | | | | 90 | 100 | 100 | 95 | | |
| 2 | 4.48 | 24 | | | | | 55 | 45 | 75 | 75 | | |
| 2 | 4.48 | 25 | | | | | 55 | 65 | 65 | 90 | | |
| 2 | 6.72 | 26 | | | | | 100 | 75 | 100 | 90 | | |
| 2 | 4.48 | 27 | | | | | 20 | 60 | 95 | 90 | | |
| 2 | 4.48 | 28 | | | | | 65 | 60 | 95 | 90 | | |
| 3 | 2.24 | 23 | 80 | 90 | 80 | 100 | | | | | | |
| 3 | 2.24 | 24 | 60 | 90 | 35 | 55 | | | | | | |
| 3 | 2.24 | 25 | 100 | 100 | 55 | 70 | | | | | | |
| 3 | 2.24 | 26 | 100 | 95 | 100 | 90 | | | | | | |
| 3 | 2.24 | 27 | 90 | 75 | 75 | 75 | | | | | | |
| 3 | 2.24 | 28 | 65 | 75 | 90 | 75 | | | | | | |

EXAMPLE 3

Additional treatments on grain sorghum were conducted by varying the rate of safener application and using Herbicide 3 at two different rates of application. The "Percent Plant Inhibition" was determined as described in Example 2. Results of these additional treatments are set forth in Table 3.

TABLE 3

| Herbicide | Safener | | % Plant Inhibition | |
|---|---|---|---|---|
| Rate | No. | Rate | W | Wo |
| 1.1 | 8 | 2.2 | 70 | 75 |
| 2.2 | 8 | 2.2 | 95 | 80 |
| 1.1 | 8 | 4.4 | 80 | 75 |
| 2.2 | 8 | 4.4 | 45 | 80 |
| 1.1 | 9 | 2.2 | 20 | 75 |
| 2.2 | 9 | 2.2 | 65 | 80 |
| 1.1 | 9 | 4.4 | 40 | 75 |
| 2.2 | 9 | 4.4 | 50 | 80 |
| 1.1 | 10 | 2.2 | 70 | 75 |
| 2.2 | 10 | 2.2 | 90 | 80 |
| 1.1 | 10 | 4.4 | 80 | 75 |
| 2.2 | 10 | 4.4 | 90 | 80 |
| 1.1 | 16 | 2.2 | 80 | 75 |
| 2.2 | 16 | 2.2 | 60 | 80 |
| 1.1 | 16 | 4.4 | 45 | 75 |
| 2.2 | 16 | 4.4 | 60 | 80 |
| 1.1 | 11 | 2.2 | 80 | 75 |
| 2.2 | 11 | 2.2 | 70 | 80 |
| 1.1 | 11 | 4.4 | 50 | 75 |
| 2.2 | 11 | 4.4 | 60 | 80 |
| 1.1 | 12 | 2.2 | 80 | 75 |
| 2.2 | 12 | 2.2 | 90 | 80 |
| 1.1 | 12 | 4.4 | 90 | 75 |
| 2.2 | 12 | 4.4 | 95 | 80 |
| 1.1 | 13 | 2.2 | 30 | 70 |
| 2.2 | 13 | 2.2 | 90 | 80 |
| 1.1 | 13 | 4.4 | 40 | 75 |
| 2.2 | 13 | 4.4 | 85 | 80 |
| 1.1 | 14 | 2.2 | 60 | 75 |
| 2.2 | 14 | 2.2 | 90 | 80 |
| 1.1 | 14 | 4.4 | 30 | 75 |
| 2.2 | 14 | 4.4 | 60 | 80 |
| 1.1 | 15 | 2.2 | 70 | 75 |
| 2.2 | 15 | 2.2 | 60 | 80 |
| 1.1 | 15 | 4.4 | 60 | 75 |
| 2.2 | 15 | 4.4 | 80 | 80 |
| 1.1 | 17 | 2.2 | 50 | 75 |
| 2.2 | 27 | 2.2 | 80 | 80 |
| 1.1 | 17 | 4.4 | 65 | 75 |
| 2.2 | 17 | 4.4 | 80 | 80 |
| 1.1 | 18 | 2.2 | 40 | 75 |
| 2.2 | 18 | 2.2 | 90 | 80 |
| 1.1 | 18 | 4.4 | 20 | 75 |
| 2.2 | 18 | 4.4 | 50 | 80 |

EXAMPLE 4

The procedure of Example 2 was followed to determine the interaction between herbicide and safener when both are shallow incorporated in soil preemergent to the crop species. In present Example 4, however, all containers were seeded with a weed species in addition to crop seed. Results are set forth in Tables 4, 5 and 6. Herbicide and safener rates are in Kg/ha.

TABLE 4

| Herbicide | | Compound | | Wheat | | Wild Oat | |
|---|---|---|---|---|---|---|---|
| No. | Rate | No. | Rate | W | WO | W | WO |
| 1 | 0.14 | 32 | 8.96 | 5 | 60 | 85 | 95 |
| 1 | 0 | 32 | 8.96 | 20 | — | 10 | — |
| 1 | 0.56 | 32 | 8.96 | 20 | 100 | 95 | 100 |
| 1 | 0.14 | 32 | 2.24 | 5 | 60 | 90 | 95 |
| 1 | 0.56 | 32 | 2.24 | 95 | 100 | 100 | 100 |
| 1 | 0 | 32 | 2.24 | 35 | — | 10 | — |
| 1 | 0.56 | 38 | 8.96 | 75 | 100 | 100 | 100 |
| 1 | 0 | 38 | 8.96 | 10 | — | 5 | — |
| 1 | 0.125 | 38 | 8.96 | 20 | 60 | 85 | 95 |
| 1 | 0.56 | 38 | 2.24 | 95 | 100 | 100 | 100 |
| 1 | 0 | 38 | 2.24 | 5 | — | 0 | — |
| 1 | 0.14 | 38 | 2.24 | 5 | 60 | 90 | 95 |
| 1 | 0.14 | 41 | 8.96 | 15 | 60 | 90 | 95 |
| 1 | 0.56 | 41 | 8.96 | 65 | 100 | 100 | 100 |
| 1 | 0 | 41 | 8.96 | 20 | — | 5 | — |
| 1 | 0.56 | 41 | 2.24 | 10 | 100 | 95 | 100 |
| 1 | 0.14 | 41 | 2.24 | 45 | 60 | 95 | 95 |
| 1 | 0 | 41 | 2.24 | 10 | — | 0 | — |
| 1 | 0.14 | 45 | 8.96 | 25 | 20 | 95 | 95 |
| 1 | 0 | 45 | 8.96 | 15 | — | 10 | — |
| 1 | 0.56 | 45 | 8.96 | 40 | 95 | 95 | 100 |
| 1 | 0.14 | 45 | 2.24 | 10 | 20 | 95 | 95 |
| 1 | 0.56 | 45 | 2.24 | 95 | 95 | 100 | 100 |
| 1 | 0.14 | 50 | 8.96 | 0 | 70 | 45 | 95 |
| 1 | 0.56 | 50 | 8.96 | 40 | 100 | 100 | 100 |
| 1 | 0 | 50 | 8.96 | 5 | — | 80 | — |
| 1 | 0.56 | 50 | 2.24 | 100 | 100 | 100 | 100 |
| 1 | 0.14 | 50 | 2.24 | 15 | 70 | 100 | 95 |
| 1 | 0 | 50 | 2.24 | 0 | — | 20 | — |
| 1 | 0.56 | 55 | 8.96 | 40 | 90 | 100 | 100 |
| 1 | 0.56 | 55 | 2.24 | 85 | 90 | 100 | 100 |

TABLE 5

| | | | | % Plant Inhibition | | | | | | | |
|---|---|---|---|---|---|---|---|---|---|---|---|
| Herbicide | | Compound | | Rice | | Soybean | | Hemp Sesbania | | Velvetleaf | |
| No. | Rate | No. | Rate | W | WO | W | WO | W | WO | W | WO |
| 2 | 6.72 | 27 | 8.96 | 100 | 90 | 100 | 100 | 100 | 100 | 100 | 100 |
| 2 | 0 | 27 | 8.96 | 0 | — | 0 | — | 100 | — | 0 | — |
| 2 | 2.24 | 27 | 8.96 | 100 | 85 | 100 | 95 | 100 | 100 | 100 | 100 |
| 2 | 0 | 27 | 2.24 | 15 | — | 0 | — | 100 | — | 30 | — |
| 2 | 2.24 | 27 | 2.24 | 50 | 85 | 0 | 95 | 100 | 100 | 100 | 100 |
| 2 | 6.72 | 27 | 2.24 | 80 | 90 | 75 | 100 | 100 | 100 | 100 | 100 |
| 2 | 1.12 | 35 | 8.96 | 20 | 5 | 40 | 30 | 100 | 100 | 100 | 100 |
| 2 | 0 | 35 | 8.96 | 0 | — | 0 | — | 100 | — | 25 | — |
| 2 | 4.48 | 35 | 8.96 | 85 | 95 | 95 | 85 | 100 | 100 | 100 | 100 |
| 2 | 1.12 | 35 | 2.24 | 5 | 5 | 15 | 30 | 100 | 100 | 100 | 100 |
| 2 | 4.48 | 35 | 2.24 | 35 | 95 | 35 | 85 | 100 | 100 | 100 | 100 |
| 2 | 0 | 35 | 2.24 | 0 | — | 0 | — | 100 | — | 5 | — |

TABLE 6

| | | | | % Plant Inhibition | | | | | |
|---|---|---|---|---|---|---|---|---|---|
| Herbicide | | Compound | | Sorghum | | Wheat | | Green Foxtail | |
| No. | Rate | No. | Rate | W | WO | W | WO | W | WO |
| 3 | 0 | 29 | 8.96 | 15 | — | 0 | — | 25 | — |
| 3 | 2.24 | 29 | 8.96 | 90 | 95 | 10 | 55 | 100 | 95 |
| 3 | 0.56 | 29 | 8.96 | 15 | 75 | 0 | 30 | 95 | 95 |
| 3 | 0 | 29 | 2.24 | 0 | — | 10 | — | 35 | — |
| 3 | 0.56 | 29 | 2.24 | 80 | 75 | 10 | 30 | 95 | 95 |
| 3 | 2.24 | 29 | 2.24 | 100 | 95 | 40 | 55 | 100 | 95 |
| 3 | 2.24 | 30 | 8.96 | 85 | 95 | 65 | 50 | 100 | 95 |
| 3 | 0.56 | 30 | 8.96 | 80 | 85 | 5 | 30 | 95 | 90 |
| 3 | 0 | 30 | 8.96 | 10 | — | 10 | — | 10 | — |
| 3 | 0 | 30 | 2.24 | 10 | — | 20 | — | 0 | — |
| 3 | 0.56 | 30 | 2.24 | 65 | 85 | 15 | 30 | 95 | 90 |
| 3 | 2.24 | 30 | 2.24 | 100 | 95 | 20 | 50 | 95 | 95 |
| 3 | 0 | 31 | 8.96 | 5 | — | 10 | — | 30 | — |
| 3 | 2.24 | 31 | 8.96 | 95 | 95 | 75 | 65 | 100 | 95 |
| 3 | 0.56 | 31 | 8.96 | 25 | 95 | 30 | 50 | 100 | 95 |
| 3 | 0.56 | 31 | 2.24 | 75 | 95 | 80 | 50 | 100 | 95 |
| 3 | 0 | 31 | 2.24 | 20 | — | 10 | — | 70 | — |
| 3 | 2.24 | 31 | 2.24 | 100 | 95 | 80 | 65 | 100 | 95 |
| 3 | 0.56 | 34 | 8.96 | 50 | 100 | 5 | 20 | 100 | 100 |
| 3 | 0 | 34 | 8.96 | 10 | — | 5 | — | 10 | — |
| 3 | 2.24 | 34 | 8.96 | 90 | 100 | 70 | 65 | 100 | 100 |
| 3 | 0.56 | 34 | 2.24 | 85 | 100 | 10 | 20 | 100 | 100 |
| 3 | 0 | 34 | 2.24 | 5 | — | 5 | — | 0 | — |
| 3 | 2.24 | 34 | 2.24 | 100 | 100 | 70 | 65 | 100 | 100 |
| 3 | 2.24 | 36 | 8.96 | 95 | 100 | 80 | 80 | 100 | 100 |
| 3 | 0 | 36 | 8.96 | 25 | — | 5 | — | 0 | — |
| 3 | 0.56 | 36 | 8.96 | 85 | 100 | 20 | 65 | 95 | 95 |
| 3 | 0 | 36 | 2.24 | 40 | — | 0 | — | 0 | — |
| 3 | 0.56 | 36 | 2.24 | 95 | 100 | 60 | 65 | 100 | 95 |
| 3 | 2.24 | 36 | 2.24 | 100 | 100 | 90 | 80 | 100 | 100 |
| 3 | 0 | 37 | 8.96 | 0 | — | 10 | — | 15 | — |
| 3 | 0.56 | 37 | 8.96 | 55 | 100 | 10 | 40 | 100 | 95 |
| 3 | 2.24 | 37 | 8.96 | 70 | 100 | 20 | 75 | 100 | 95 |
| 3 | 0.56 | 37 | 2.24 | 95 | 100 | 25 | 40 | 100 | 95 |
| 3 | 2.24 | 37 | 2.24 | 95 | 100 | 60 | 75 | 100 | 95 |
| 3 | 0 | 37 | 2.24 | 0 | — | 0 | — | 0 | — |
| 3 | 0.56 | 41 | 8.96 | 45 | 95 | 0 | 35 | 100 | 100 |
| 3 | 2.24 | 41 | 8.96 | 95 | 100 | 50 | 90 | 100 | 100 |
| 3 | 0 | 41 | 8.96 | 5 | — | 0 | — | 0 | — |
| 3 | 2.24 | 41 | 2.24 | 100 | 100 | 95 | 90 | 100 | 100 |
| 3 | 0 | 41 | 2.24 | 0 | — | 15 | — | 0 | — |
| 3 | 0.56 | 41 | 2.24 | 95 | 95 | 20 | 35 | 100 | 100 |
| 3 | 0.56 | 43 | 8.96 | 80 | 100 | 40 | 80 | 100 | 95 |
| 3 | 0 | 43 | 8.96 | 10 | — | 0 | — | 0 | — |
| 3 | 2.24 | 43 | 8.96 | 85 | 100 | 15 | 90 | 100 | 100 |
| 3 | 0.56 | 43 | 2.24 | 100 | 100 | 65 | 80 | 95 | 95 |
| 3 | 2.24 | 43 | 2.24 | 100 | 100 | 75 | 90 | 100 | 100 |
| 3 | 0 | 43 | 2.24 | 10 | — | 35 | — | 0 | — |
| 3 | 2.24 | 45 | 8.96 | 95 | 100 | 80 | 90 | 100 | 100 |
| 3 | 0.56 | 45 | 8.96 | 95 | 95 | 0 | 35 | 100 | 100 |
| 3 | 0 | 45 | 8.96 | 0 | — | 30 | — | 0 | — |
| 3 | 2.24 | 45 | 2.24 | 100 | 100 | 85 | 90 | 100 | 100 |
| 3 | 0 | 45 | 2.24 | 15 | — | 0 | — | 0 | — |
| 3 | 0.56 | 45 | 2.24 | 95 | 95 | 70 | 35 | 100 | 100 |
| 3 | 0 | 46 | 8.96 | 0 | — | 30 | — | 0 | — |
| 3 | 2.24 | 46 | 8.96 | 95 | 100 | 85 | 90 | 100 | 100 |
| 3 | 0.56 | 46 | 8.96 | 80 | 100 | 25 | 80 | 100 | 95 |
| 3 | 0.56 | 46 | 2.24 | 100 | 100 | 60 | 80 | 100 | 95 |
| 3 | 0 | 46 | 2.24 | 10 | — | 10 | — | 0 | — |
| 3 | 2.24 | 46 | 2.24 | 95 | 100 | 95 | 90 | 100 | 100 |
| 3 | 0 | 54 | 8.96 | | | 15 | — | 0 | — |
| 3 | 2.24 | 54 | 8.96 | | | 40 | 80 | 100 | 100 |
| 3 | 0.56 | 54 | 8.96 | | | 0 | 60 | 95 | 100 |
| 3 | 0.56 | 54 | 2.24 | | | 40 | 60 | 100 | 100 |
| 3 | 2.24 | 54 | 2.24 | | | 90 | 80 | 100 | 100 |

TABLE 6-continued

| Herbicide | | Compound | | Sorghum | | Wheat | | Green Foxtail | |
|---|---|---|---|---|---|---|---|---|---|
| No. | Rate | No. | Rate | W | WO | W | WO | W | WO |
| 3 | 0 | 54 | 2.24 | 0 | — | | | 0 | — |
| 3 | 2.24 | 54 | 8.96 | 100 | 95 | | | 100 | 100 |
| 3 | 0 | 54 | 8.96 | 10 | — | | | 0 | — |
| 3 | 0.56 | 54 | 8.96 | 90 | 95 | | | 100 | 100 |
| 3 | 0.56 | 54 | 2.24 | 95 | 95 | | | 100 | 100 |
| 3 | 2.24 | 54 | 2.24 | 100 | 95 | | | 100 | 100 |
| 3 | 0 | 54 | 2.24 | 10 | — | | | 0 | — |
| 3 | 0.56 | 55 | 8.96 | 60 | 90 | | | 100 | 100 |
| 3 | 2.24 | 55 | 8.96 | 65 | 95 | | | 100 | 100 |
| 3 | 0 | 55 | 8.96 | 60 | — | | | 100 | — |
| 3 | 2.24 | 55 | 2.24 | 80 | 95 | | | 100 | 100 |
| 3 | 0.56 | 55 | 2.24 | 30 | 90 | | | 100 | 100 |
| 3 | 0 | 55 | 2.24 | 0 | — | | | 0 | — |
| 3 | 2.24 | 55 | 8.96 | | | 20 | 80 | 100 | 100 |
| 3 | 2.24 | 55 | 2.24 | | | 60 | 80 | 100 | 100 |

TABLE 7

| Herbicide | | Compound | | Wheat | | Wild Oat | |
|---|---|---|---|---|---|---|---|
| No. | Rate | No. | Rate | W | Wo | W | Wo |
| 1 | 0.56 | 41 | 2.24 | 95 | 98 | 100 | 100 |
| 1 | 1.12 | 41 | 2.24 | 100 | 100 | 100 | 100 |
| 1 | 0 | 41 | 2.24 | 15 | — | 0 | — |
| 1 | 0.28 | 41 | 2.24 | 90 | 90 | 100 | 100 |
| 1 | 0 | 41 | 0.56 | 38 | — | 0 | — |
| 1 | 0.28 | 41 | 0.56 | 95 | 90 | 100 | 100 |
| 1 | 0.56 | 41 | 0.56 | 98 | 98 | 100 | 100 |
| 1 | 1.12 | 41 | 0.56 | 100 | 100 | 100 | 100 |
| 1 | 0.56 | 41 | 0.14 | 98 | 98 | 100 | 100 |
| 1 | 1.12 | 41 | 0.14 | 100 | 100 | 100 | 100 |
| 1 | 0.28 | 41 | 0.14 | 93 | 90 | 100 | 100 |

TABLE 8

| Herbicide | | Compound | | Rice | | Soybean | | Velvet Leaf | | Morning Glory | |
|---|---|---|---|---|---|---|---|---|---|---|---|
| No. | Rate | No. | Rate | W | Wo | W | Wo | W | Wo | W | Wo |
| 2 | 0 | 27 | 3.36 | 0 | — | | | | | 0 | — |
| 2 | 6.72 | 27 | 3.36 | 100 | 100 | | | | | 98 | 98 |
| 2 | 3.36 | 27 | 3.36 | 100 | 98 | | | | | 98 | 98 |
| 2 | 0.17 | 27 | 3.36 | 100 | 98 | | | | | 100 | 97 |
| 2 | 0 | 27 | 1.68 | 0 | — | | | | | 0 | — |
| 2 | 0.17 | 27 | 1.68 | 98 | 98 | | | | | 90 | 97 |
| 2 | 3.36 | 27 | 1.68 | 100 | 98 | | | | | 98 | 98 |
| 2 | 6.72 | 27 | 1.68 | 98 | 100 | | | | | 100 | 98 |
| 2 | 6.72 | 27 | 0.84 | 100 | 100 | | | | | 100 | 98 |
| 2 | 0.17 | 27 | 0.84 | 95 | 98 | | | | | 95 | 97 |
| 2 | 6.72 | 35 | 2.24 | | | 100 | 100 | 100 | 100 | 95 | 95 |
| 2 | 3.36 | 35 | 2.24 | | | 95 | 95 | 100 | 100 | 98 | 95 |
| 2 | 1.68 | 35 | 2.24 | | | 80 | 78 | 100 | 100 | 80 | 95 |
| 2 | 0 | 35 | 2.24 | | | 0 | — | 0 | — | 0 | — |
| 2 | 0 | 35 | 0.56 | | | 0 | — | 0 | — | 10 | — |
| 2 | 1.68 | 35 | 0.56 | | | 53 | 78 | 100 | 100 | 75 | 95 |
| 2 | 3.36 | 35 | 0.56 | | | 95 | 95 | 100 | 100 | 95 | 95 |
| 2 | 6.72 | 35 | 0.56 | | | 100 | 100 | 100 | 95 | 100 | 100 |
| 2 | 6.72 | 35 | 0.14 | | | 100 | 100 | 98 | 100 | 100 | 95 |
| 2 | 3.36 | 35 | 0.14 | | | 65 | 95 | 100 | 100 | 85 | 95 |
| 2 | 1.68 | 35 | 0.14 | | | 95 | 78 | 100 | 100 | 80 | 95 |

EXAMPLE 5

The following procedure was used to determine the interaction between a herbicide and safener when applied as a tank mix before emergence of the crop and weed species. Containers were filled and compacted with fumigated Ray silt loam top soil to a depth of about 1.3 cm from the top of the container. A first container was designated as a blank, a second container was designated as a herbicide control, and a third container was designated as a herbicide-safener test container. Each of the containers was seeded with both crop plant and weed species. The herbicide-safener tank mix was applied to the seeded containers either by a procedure of topical application to a soil layer placed over the seed bed followed by watering to achieve incorporation, or by a procedure of incorporation of a quantity of the tank mix into soil and then placement of the treated soil into the container over the seed bed. The containers were then placed on a sand bench in a greenhouse and watered by subirrigation. Plant response was observed about three weeks after initial treatment to determine "Percent Plant Inhibition" in the manner explained in Example 2. Results as reported in Tables 7, 8, and 9 are averages of duplicate observations. Herbicide and safener rates are given in kg/ha.

TABLE 9

| Herbicide | | Compound | | Wheat | | Downy Brome | | Green Foxtail | |
|---|---|---|---|---|---|---|---|---|---|
| No. | Rate | No. | Rate | W | Wo | W | Wo | W | Wo |
| 3 | 4.48 | 30 | 2.24 | 80 | 88 | 95 | 95 | 100 | 100 |
| 3 | 2.24 | 30 | 2.24 | 53 | 80 | 85 | 95 | 100 | 100 |
| 3 | 1.12 | 30 | 2.24 | 38 | 50 | 85 | 75 | 100 | 100 |
| 3 | 0 | 30 | 2.24 | 8 | — | 0 | — | 0 | — |
| 3 | 4.48 | 30 | 0.56 | 65 | 88 | 75 | 95 | 95 | 100 |
| 3 | 2.24 | 30 | 0.56 | 58 | 80 | 90 | 95 | 100 | 100 |
| 3 | 1.12 | 30 | 0.56 | 33 | 50 | 85 | 75 | 100 | 100 |
| 3 | 0 | 30 | 0.56 | 0 | — | 0 | — | 0 | — |
| 3 | 4.48 | 30 | 0.14 | 80 | 88 | 90 | 95 | 100 | 100 |
| 3 | 2.24 | 30 | 0.14 | 60 | 80 | 90 | 95 | 100 | 100 |
| 3 | 1.12 | 30 | 0.14 | 43 | 50 | 85 | 75 | 98 | 100 |

EXAMPLE 6

The following procedure was used to determine the interaction between a herbicide and safener when the herbicide is topically applied to the soil surface and the safener is applied to crop seed. Crop plant seed was treated with the safener either by contacting the seed with safener in powder form or by contacting the seed with a solution or suspension of safener compound dissolved or suspended in a suitable solvent, typically methylene chloride or toluene. Relative amounts of safener compound and seed were used to provide a safener-on-seed concentration, on a percent weight/- weight basis, of 0.031 wt.%, 0.125 wt.%, and 0.5 wt.%. Containers were filled and compacted with fumigated Ray silt loam type soil to a depth of about 1.3 cm from the top of the container. A first container was designated as a blank, a second container was designated as a herbicide control, and a third container was designated as a herbicide-safener test container. Untreated crop seed was placed in the first and second containers. Safener-treated crop seed was placed in the third container. The containers were then filled to the top with soil and leveled to form a soil cover layer. To the second and third containers the appropriate herbicide was sprayed onto the surface of the soil cover layer. All containers were given about 0.6 cm of overhead water to simulate an activating rainfall. The containers were placed on a greenhouse sand bench and subirrigated as required for the duration of the test. Plant response was observed about three weeks after initial treatment to determine "Percent Plant Inhibition" in the manner explained in Example 2. Results are set forth in Table 10. Herbicide rate is given in kg/ha and safener rate is given in percent weight/weight of safener/seed.

TABLE 10

| Herbicide | | Compound | | % Plant Inhibition Wheat | |
|---|---|---|---|---|---|
| No. | Rate | No. | Rate | W | Wo |
| 1 | 0.28 | 32 | 0.5 | 50 | 88 |
| 1 | 0.56 | 32 | 0.5 | 65 | 95 |
| 1 | 0.56 | 32 | 0.125 | 70 | 95 |
| 1 | 0.28 | 32 | 0.125 | 0 | 88 |
| 1 | 0.28 | 32 | 0.031 | 70 | 88 |
| 1 | 0.56 | 32 | 0.031 | 90 | 95 |
| 1 | 0.56 | 32 | 0.5 | 50 | 88 |
| 1 | 0 | 32 | 0.5 | 60 | — |
| 1 | 0.56 | 32 | 0.5 | 65 | 95 |
| 1 | 0.56 | 32 | 0.125 | 70 | 95 |
| 1 | 0 | 32 | 0.125 | 20 | — |
| 1 | 0.28 | 32 | 0.125 | 0 | 88 |
| 1 | 0.28 | 32 | 0.031 | 70 | 88 |
| 1 | 0.56 | 32 | 0.031 | 90 | 95 |
| 1 | 0 | 33 | 0.5 | 70 | — |
| 1 | 0.56 | 33 | 0.5 | 80 | 95 |
| 1 | 0.28 | 33 | 0.5 | 45 | 88 |
| 1 | 0 | 33 | 0.125 | 30 | — |
| 1 | 0.56 | 33 | 0.125 | 90 | 95 |
| 1 | 0.28 | 33 | 0.125 | 70 | 88 |
| 1 | 0.56 | 33 | 0.031 | 95 | 95 |
| 1 | 0.28 | 33 | 0.031 | 80 | 88 |
| 1 | 0 | 38 | 0.5 | 25 | — |
| 1 | 0.28 | 38 | 0.5 | 0 | 88 |
| 1 | 0.56 | 38 | 0.5 | 15 | 95 |
| 1 | 0 | 38 | 0.125 | 20 | — |
| 1 | 0.28 | 38 | 0.125 | 10 | 88 |
| 1 | 0.56 | 38 | 0.125 | 35 | 95 |
| 1 | 0.28 | 38 | 0.031 | 35 | 88 |
| 1 | 0.56 | 38 | 0.031 | 85 | 95 |
| 1 | 0 | 39 | 0.5 | 25 | — |
| 1 | 0.28 | 39 | 0.5 | 90 | 88 |
| 1 | 0.56 | 39 | 0.5 | 95 | 95 |
| 1 | 0 | 39 | 0.125 | 0 | — |
| 1 | 0.28 | 39 | 0.125 | 75 | 88 |
| 1 | 0.56 | 39 | 0.125 | 95 | 95 |
| 1 | 0.28 | 39 | 0.031 | 85 | 88 |
| 1 | 0.56 | 39 | 0.031 | 95 | 95 |
| 1 | 0 | 45 | 0.5 | 55 | — |
| 1 | 0.28 | 45 | 0.5 | 35 | 88 |
| 1 | 0.56 | 45 | 0.5 | 45 | 95 |
| 1 | 0 | 45 | 0.125 | 0 | — |

TABLE 10-continued

| Herbicide | | Compound | | % Plant Inhibition Wheat | |
|---|---|---|---|---|---|
| No. | Rate | No. | Rate | W | Wo |
| 1 | 0.14 | 45 | 0.125 | 5 | 88 |
| 1 | 0.56 | 45 | 0.125 | 25 | 95 |
| 1 | 0.28 | 45 | 0.031 | 30 | 88 |
| 1 | 0.56 | 45 | 0.031 | 85 | 95 |
| 3 | 2.24 | 32 | 0.5 | 95 | 92 |
| 3 | 0.56 | 32 | 0.5 | 85 | 73 |
| 3 | 0.56 | 32 | 0.125 | 60 | 73 |
| 3 | 2.24 | 32 | 0.125 | 95 | 92 |
| 3 | 2.24 | 32 | 0.031 | 95 | 92 |
| 3 | 0.56 | 32 | 0.031 | 50 | 73 |
| 3 | 2.24 | 33 | 0.5 | 95 | 92 |
| 3 | 0.56 | 33 | 0.5 | 80 | 73 |
| 3 | 2.24 | 33 | 0.125 | 95 | 92 |
| 3 | 0.56 | 33 | 0.125 | 80 | 73 |
| 3 | 0.56 | 33 | 0.031 | 90 | 73 |
| 3 | 2.24 | 33 | 0.031 | 100 | 92 |
| 3 | 2.24 | 38 | 0.5 | 90 | 92 |
| 3 | 0.56 | 38 | 0.5 | 65 | 73 |
| 3 | 0.56 | 38 | 0.125 | 55 | 73 |
| 3 | 2.24 | 38 | 0.125 | 95 | 92 |
| 3 | 2.24 | 38 | 0.031 | 95 | 92 |
| 3 | 0.56 | 38 | 0.031 | 45 | 73 |
| 3 | 2.24 | 39 | 0.5 | 100 | 92 |
| 3 | 0.56 | 39 | 0.5 | 75 | 73 |
| 3 | 2.24 | 39 | 0.125 | 90 | 92 |
| 3 | 0.56 | 39 | 0.125 | 75 | 73 |
| 3 | 2.24 | 39 | 0.031 | 95 | 92 |
| 3 | 0.56 | 39 | 0.031 | 80 | 73 |
| 3 | 2.24 | 45 | 0.5 | 85 | 92 |
| 3 | 0.56 | 45 | 0.5 | 60 | 73 |
| 3 | 2.24 | 45 | 0.125 | 80 | 92 |
| 3 | 0.56 | 45 | 0.125 | 55 | 73 |
| 3 | 2.24 | 45 | 0.031 | 80 | 92 |
| 3 | 0.56 | 45 | 0.031 | 45 | 73 |

EXAMPLE 7

The following procedure was used to determine the interaction between a herbicide and safener when the safener is applied in the soil furrow containing crop seed and the herbicide is incorporated in the soil corner layer. Containers were filled and compacted with fumigated ray silt loam type soil to a depth of about 1.3 cm from the top of the container. A first container was designated as a blank, a second container was designated as a herbicide control, and a third container was designated as a herbicide safener test container. Each container was seeded with crop seed in marked furrows. Safener compound, dissolved in an appropriate solvent, was applied directly to the seeded furrows of the third container. Then, each of the second and third containers was filled and leveled with a cover layer of soil having incorporated therein the selected herbicide. The first container was filled and leveled with soil containing no herbicide. The containers were then placed on a greenhouse sand bench and subirrigated as required for the duration of the test. Plant response was observed about three weeks after initial treatment to determine "Percent Plant Inhibition" in the manner explained in Example 2. Results are set forth in Table 11. Herbicide rate is given in kg/ha. The safener rate for all compounds in Table 11 was at 0.28 kg/ha.

TABLE 11

| Herbicide | | Compound | % Plant Inhibition | | | | | | | | |
|---|---|---|---|---|---|---|---|---|---|---|---|
| | | | Sorghum | | Wheat | | Rice | | Soybean | | Corn | |
| No. | Rate | No. | W | Wo | W | Wo | W | Wo | W | Wo | W | Wo |
| 1 | 0.56 | 29 | | | 80 | 90 | | | | | | |
| 1 | 0.56 | 30 | | | 80 | 100 | | | | | | |
| 1 | 0.56 | 31 | | | 75 | 95 | | | | | | |

TABLE 11-continued

| | | | % Plant Inhibition | | | | | | | | |
|---|---|---|---|---|---|---|---|---|---|---|---|
| Herbicide | | Compound | Sorghum | | Wheat | | Rice | | Soybean | | Corn | |
| No. | Rate | No. | W | Wo | W | Wo | W | Wo | W | Wo | W | Wo |
| 1 | 0.56 | 32 | | | 20 | 100 | | | | | | |
| 1 | 0.56 | 33 | | | 65 | 95 | | | | | | |
| 1 | 0.56 | 34 | | | 70 | 95 | | | | | | |
| 1 | 0.56 | 35 | | | 95 | 95 | | | | | | |
| 1 | 0.56 | 36 | | | 85 | 95 | | | | | | |
| 1 | 0.56 | 37 | | | 95 | 100 | | | | | | |
| 1 | 0.56 | 38 | | | 30 | 100 | | | | | | |
| 1 | 0.56 | 39 | | | 90 | 95 | | | | | | |
| 1 | 0.56 | 40 | | | 65 | 95 | | | | | | |
| 1 | 0.56 | 41 | | | 50 | 100 | | | | | | |
| 1 | 0.56 | 42 | | | 95 | 100 | | | | | | |
| 1 | 0.56 | 43 | | | 60 | 95 | | | | | | |
| 1 | 0.56 | 44 | | | 90 | 95 | | | | | | |
| 1 | 0.56 | 45 | | | 30 | 95 | | | | | | |
| 1 | 0.56 | 46 | | | 95 | 95 | | | | | | |
| 1 | 0.56 | 47 | | | 95 | 95 | | | | | | |
| 1 | 0.56 | 48 | | | 70 | 95 | | | | | | |
| 1 | 0.56 | 49 | | | 90 | 95 | | | | | | |
| 1 | 0.56 | 50 | | | 45 | 95 | | | | | | |
| 1 | 0.56 | 52 | | | 95 | 95 | | | | | | |
| 1 | 0.56 | 53 | | | 90 | 95 | | | | | | |
| 1 | 0.56 | 54 | | | 90 | 100 | | | | | | |
| 1 | 0.56 | 55 | | | 95 | 100 | | | | | | |
| 1 | 0.56 | 56 | | | 95 | 95 | | | | | | |
| 1 | 0.56 | 57 | | | 80 | 100 | | | | | | |
| 1 | 0.56 | 58 | | | 40 | 95 | | | | | | |
| 1 | 0.56 | 59 | | | 75 | 100 | | | | | | |
| 1 | 0.56 | 60 | | | 90 | 95 | | | | | | |
| 1 | 0.56 | 61 | | | 85 | 100 | | | | | | |
| 1 | 0.56 | 62 | | | 50 | 90 | | | | | | |
| 1 | 0.56 | 63 | | | 90 | 100 | | | | | | |
| 2 | 6.72 | 29 | | | | | 80 | 70 | 70 | 55 | | |
| 2 | 6.72 | 30 | | | | | 75 | 80 | 70 | 70 | | |
| 2 | 6.72 | 31 | | | | | 100 | 95 | 100 | 95 | | |
| 2 | 6.72 | 32 | | | | | 100 | 100 | 100 | 95 | | |
| 2 | 6.72 | 33 | | | | | 100 | 80 | 90 | 90 | | |
| 2 | 6.72 | 34 | | | | | 100 | 100 | 100 | 95 | | |
| 2 | 6.72 | 35 | | | | | 50 | 90 | 40 | 90 | | |
| 2 | 6.72 | 36 | | | | | 100 | 90 | 100 | 90 | | |
| 2 | 6.72 | 37 | | | | | 100 | 100 | 100 | 95 | | |
| 2 | 6.72 | 38 | | | | | 100 | 100 | 100 | 95 | | |
| 2 | 6.72 | 39 | | | | | 90 | 100 | 100 | 95 | | |
| 2 | 6.72 | 40 | | | | | 95 | 100 | 100 | 95 | | |
| 2 | 6.72 | 41 | | | | | 100 | 100 | 95 | 100 | | |
| 2 | 6.72 | 42 | | | | | 100 | 100 | 100 | 100 | | |
| 2 | 4.48 | 43 | | | | | 100 | 95 | 95 | 95 | | |
| 2 | 4.48 | 44 | | | | | 80 | 95 | 95 | 95 | | |
| 2 | 4.48 | 45 | | | | | 100 | 90 | 85 | 75 | | |
| 2 | 4.48 | 46 | | | | | 100 | 100 | 100 | 100 | | |
| 2 | 4.48 | 47 | | | | | 60 | 60 | 100 | 95 | | |
| 2 | 4.48 | 48 | | | | | 70 | 75 | 90 | 85 | | |
| 2 | 4.48 | 49 | | | | | 70 | 75 | 100 | 85 | | |
| 2 | 4.48 | 50 | | | | | 60 | 75 | 100 | 85 | | |
| 2 | 6.72 | 51 | | | | | 60 | 70 | 100 | 95 | | |
| 2 | 6.72 | 52 | | | | | 70 | 90 | 95 | 100 | | |
| 2 | 6.72 | 53 | | | | | 75 | 90 | 100 | 100 | | |
| 2 | 6.72 | 54 | | | | | | | 100 | 100 | | |
| 2 | 6.72 | 55 | | | | | 80 | 85 | 100 | 90 | | |
| 2 | 6.72 | 56 | | | | | | | 90 | 85 | | |
| 2 | 6.72 | 57 | | | | | | | 70 | 70 | | |
| 2 | 6.72 | 58 | | | | | | | 100 | 100 | | |
| 2 | 6.72 | 59 | | | | | | | 75 | 90 | | |
| 2 | 6.72 | 60 | | | | | | | 100 | 95 | | |
| 2 | 6.72 | 61 | | | | | | | 100 | 95 | | |
| 2 | 4.48 | 62 | | | | | | | 100 | 80 | | |
| 2 | 6.72 | 63 | | | | | | | 100 | 100 | | |
| 3 | 2.24 | 29 | 20 | 85 | 20 | 65 | | | | | | |
| 3 | 2.24 | 30 | 10 | 90 | 20 | 60 | | | | | | |
| 3 | 2.24 | 31 | 90 | 100 | 20 | 80 | | | | | | |
| 3 | 2.24 | 32 | 75 | 100 | 40 | 60 | | | | | | |
| 3 | 2.24 | 33 | 85 | 85 | 50 | 75 | | | | | | |
| 3 | 2.24 | 34 | 45 | 100 | 50 | 90 | | | | | | |
| 3 | 2.24 | 35 | 95 | 100 | 65 | 85 | | | | | | |
| 3 | 2.24 | 36 | 30 | 100 | 20 | 85 | | | | | | |
| 3 | 2.24 | 37 | 30 | 95 | 40 | 80 | | | | | | |
| 3 | 2.24 | 38 | 80 | 95 | 50 | 80 | | | | | | |
| 3 | 2.24 | 39 | 95 | 100 | 100 | 90 | | | | | | |
| 3 | 2.24 | 40 | 95 | 100 | 85 | 90 | | | | | | |

TABLE 11-continued

| Herbicide | | Compound | % Plant Inhibition | | | | | | | | | |
| --- | --- | --- | --- | --- | --- | --- | --- | --- | --- | --- | --- | --- |
| | | | Sorghum | | Wheat | | Rice | | Soybean | | Corn | |
| No. | Rate | No. | W | Wo | W | Wo | W | Wo | W | Wo | W | Wo |
| 3 | 2.24 | 41 | 60 | 95 | 25 | 60 | | | | | | |
| 3 | 2.24 | 42 | 60 | 95 | 100 | 60 | | | | | | |
| 3 | 2.24 | 43 | 60 | 100 | 30 | 70 | | | | | | |
| 3 | 2.24 | 44 | 90 | 100 | 55 | 70 | | | | | | |
| 3 | 2.24 | 45 | 90 | 95 | 40 | 75 | | | | | | |
| 3 | 2.24 | 46 | 80 | 100 | 10 | 75 | | | | | | |
| 3 | 2.24 | 47 | 100 | 100 | 95 | 90 | | | | | | |
| 3 | 2.24 | 48 | 100 | 100 | 65 | 95 | | | | | | |
| 3 | 2.24 | 49 | 100 | 100 | 85 | 95 | | | | | | |
| 3 | 2.24 | 50 | 65 | 100 | 80 | 95 | | | | | | |
| 3 | 2.24 | 51 | 100 | 100 | 85 | 95 | | | | | | |
| 3 | 2.24 | 52 | 100 | 100 | 95 | 95 | | | | | | |
| 3 | 2.24 | 53 | 100 | 100 | 100 | 95 | | | | | | |
| 3 | 2.24 | 54 | 50 | 100 | 40 | 80 | | | | | | |
| 3 | 2.24 | 55 | 60 | 100 | 80 | 80 | | | | | | |
| 3 | 2.24 | 56 | 95 | 100 | 90 | 100 | | | | | | |
| 3 | 2.24 | 57 | 30 | 55 | 90 | 100 | | | | | | |
| 3 | 2.24 | 58 | 100 | 100 | 85 | 100 | | | | | | |
| 3 | 2.24 | 59 | 100 | 100 | 70 | 95 | | | | | | |
| 3 | 2.24 | 60 | 65 | 85 | 85 | 65 | | | | | | |
| 3 | 2.24 | 61 | 80 | 100 | 80 | 85 | | | | | | |
| 3 | 2.24 | 62 | 100 | 100 | 50 | 75 | | | | | | |
| 3 | 2.24 | 63 | 100 | 100 | 90 | 90 | | | | | | |

The above examples illustrate that the cyclopropanecarbonitrile compounds of the present invention are useful in reducing herbicidal injury to certain crop plants. As indicated above, the safening agents may be applied to the plant locus as a mixture, i.e., a mixture of a herbicidally-effective amount of herbicide and a safening-effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weed to be inhibited, herbicide used, etc., but normally a herbicide-to-safening agent ratio ranging from 1:25-to-50:1 (preferably 1:5-to-15:1) parts by weight may be employed.

The amount of herbicide employed in the practice of the present invention will be at least an effective herbicidal amount. In general, effective herbicidal amounts are in the range of 0.2 and 12 kilograms/hectare. The preferred range of rate of application is from 0.4 to about 10 kg/h. It will be appreciated that at times amounts either below or above these ranges will be necessary to obtain the best results. The selection of the herbicide to inhibit the emergence and growth of weeds depends upon the species weeds to be controlled and the crop.

The herbicide, safening agent, or mixture thereof may be applied to the plant locus alone or the herbicide, safening agent, or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers, and conditioning agents to provide compositions in the form of finely-divided particulate solids, granules, pellets, wettable powders, dusts, solutions, and aqueous dispersions or emulsions. Thus, the mixture may include an adjuvant such as a finely-divided particulate solid, a solvent liquid or organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fuller's earth, sulfur, powdered cork, powdered wood, walnut flour, chalk, tobacco dust, charcoal, and the like. Typical liquid diluents useful include, for example, Stoddard solvent, acetone, methylene chloride, alcohols, glycols, ethyl acetate, benzene, and the like. Such compositions, particularly liquids and wettable powders, usually contain as a conditioning agent one or more surface-active agent in amounts sufficient to render a given composition readily dispersible in water or in oil. By the term "surface-active agent," it is understood that wetting agents, dispersing agents, suspending agents, and emulsifying agents are included therein. Such surface-active agents are well known and reference is made to U.S. Pat. No. 2,547,724, Columns 3 and 4, for detailed examples of same.

Compositions of this invention generally contain from about 5 to 95 parts herbicide and safening agents, about 1 to 50 parts surface-active agent, and about 4 to 94 parts solvent, all parts being by weight based on the total weight of the composition.

The application of the herbicide, safening agent, or mixture thereof in a liquid or particulate solid form can be carried out by conventional techniques utilizing, for example, hand-carried or tractor-mounted spreaders, power dusters, boom and hand sprayers, spray dusters, and granular applicators. The compositions can also be applied from aircraft as a dust or spray. If desired, application of the compositions of the invention to plants can be accomplished by incorporating the compositions in the soil or other media.

The crop may be protected by treating the crop seed with an effective amount of safening agent prior to planting. Generally, smaller amounts of safening agent are required to treat such seeds. A weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the compound preferably is formulated as an organic solution, powder, emulsifiable concentrate, solution, or flowable formulation which can be diluted with water by the seed treater for use in seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating composition containing one or more of the described active safening agents intimately dispersed in an inert carrier or diluent for the intended use. Such carriers may be either solids, such as talc, clay, diatomaceous earth, sawdust, calcium carbonate, and the like, or liquids such as water, kerosene, acetone, benzene, toluene, xylene, and the like, in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal, higher alkylarylsulfonates such as sodium dodecylbenzenesulfonate, and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols, and mercaptans.

The following examples illustrate the preparation of commercial seed treating compositions of the present invention:

EXAMPLE 8

The ingredients set forth in Table 12 are blended to form an emulsifiable concentrate. The resulting mixture, after proper dilution, can be applied to plant loci where safening of such plants against the adverse effects of weed herbicides is desired. The ingredients are given as weight percents.

TABLE 12

| Ingredients | Compound 2 | Compound 11 | Compound 17 | Compound 20 |
|---|---|---|---|---|
| Safener | 33.0 | 35.0 | 34.0 | 35.0 |
| ATLOX* 3409F | 3.2 | | | |
| ATLOX 3404F | 1.8 | | | |
| ATLOX 3437F | | 4.8 | 4.0 | 2.5 |
| ATLOX 3438F | | | | |
| Calcium dodecylbenzylsulfonate | | 0.2 | 1.0 | 2.5 |
| Cyclohexanone | 62.0 | | | |
| Butyl acetate | | 60.0 | | |
| C9 Aromatics | | | | 60.0 |
| Isophorone | | | 61.0 | |

*Proprietary agricultural chemical emulsifiers.

EXAMPLE 9

The ingredients set forth in Table 13 are blended and then ground using a media mill to prepare flowable safening formulations. The resulting formulations can be used to treat the selected seeds by conventional means.

TABLE 13

| Ingredients | Compound 3 | Compound 4 | Compound 5 | Compound 7 | Compound 8 | Compound 17 |
|---|---|---|---|---|---|---|
| Safener | 38.0 | 40.0 | 35.0 | 40.0 | 45.0 | 37.0 |
| Kaolin | 2.0 | 1.8 | 2.3 | 1.8 | 1.3 | 2.0 |
| Silica (finely divided) | 2.0 | 2.5 | 2.2 | 2.5 | 2.3 | 3.0 |
| Sodium Lignosulfonate | | 3.2 | 3.0 | 3.5 | 4.0 | 2.8 |
| Sodium N—Methyl-N—Oleyl Taurate | | 2.0 | 2.2 | 2.0 | 1.8 | 2.0 |
| Polyethylene Glycol | 9.0 | | | | | |
| Ethylene Glycol Methyl Cellulose | 4.0 | | 0.3 | | | 0.3 |
| Water | 45.0 | 50.5 | 55.0 | 50.2 | 45.6 | 52.9 |

EXAMPLE 10

The ingredients set forth in Table 14 are blended, and the blended composition can be applied to seeds to be treated via mist application or by tumbling.

TABLE 14

| Ingredients | Compound 1 | Compound 6 | Compound 9 | Compound 10 | Compound 12 | Compound 13 | Compound 15 | Compound 16 | Compound 18 | Compound 19 |
|---|---|---|---|---|---|---|---|---|---|---|
| Safener | 25 | 25 | 20 | 25 | 18 | 25 | 25 | 25 | 28 | 24 |
| Diethylene Glycol Monoethyl Ether | 75 | 75 | | | | | | | | 76 |
| Dimethylene Glycol Monomethyl Ether | | | 80 | | | | 75 | 75 | 72 | |
| Dibutyl Glycol Monobutyl Ether | | | | | 82 | | | | | |
| Diacetate of Diethylene Glycol Monoethyl Ether | | | | 75 | | 75 | | | | |

Although this invention has been described with respect to specific embodiments, the details thereof are

What is claimed is:

1. A compound having the structural formula:

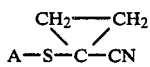

wherein A is selected from the group consisting of naphthalenyl, tetrahydronaphthalenyl, benzodioxol, and

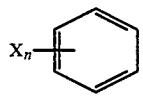

wherein X is independently selected from the group consisting of halogen, haloalkyl, alkyl, alkenyl, alkoxy, alkylthio, alkylcarbonyl, alkylalkenyl, and cycloalkyl; and n is a whole number from 1 through 5.

2. The compound of claim 1 wherein X is $CF_3$ and n is 1.
3. The compound of claim 1 wherein X is Cl and n is 1.
4. The compound of claim 1 wherein X is Cl and n is 2.
5. The compound of claim 1 wherein X is Cl and n is 3.
6. The compound of claim 1 wherein X is F and n is 1.
7. The compound of claim 1 wherein X is Br and n is 1.
8. The compound of claim 1 wherein X is t-butyl and n is 1.
9. The compound of claim 1 wherein X is methoxy and n is 1.
10. The compound of claim 1 wherein X is isopropyl and n is 1.
11. The compound of claim 1 wherein X is methyl and n is 1.
12. The compound of claim 1 wherein X is ethyl and n is 1.
13. The compound of claim 1 wherein X is methyl and n is 2.
14. The compound of claim 1 wherein X is $CF_3$ and n is 2.
15. A method of reducing injury to crop plants due to the application thereto of at least one weed herbicide which comprises applying to the plant locus a safening-effective amount of at least one compound having the structural formula:

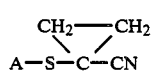

wherein A is selected from the group consisting of naphthalenyl, tetrahydronaphthalenyl, benzodioxol, and

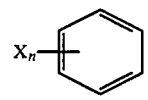

wherein X is independently selected from the group consisting of halogen, haloalkyl, alkyl, alkenyl, alkoxy, alkylthio, alkylcarbonyl, alkylalkenyl, and cycloalkyl; and n is 0 or a whole number from 1 through 5.

16. The method of claim 15 wherein X is $CF_3$ and n is 1.
17. The method of claim 15 wherein X is Cl and n is 1.
18. The method of claim 15 wherein X is Cl and n is 2.
19. The method of claim 15 wherein X is Cl and n is 3.
20. The method of claim 15 wherein X is F and n is 1.
21. The method of claim 15 wherein X is Br and n is 1.
22. The method of claim 15 wherein X is t-butyl and n is 1.
23. The method of claim 15 wherein X is methoxy and n is 1.
24. The method of claim 15 wherein X is isopropyl and n is 1.
25. The method of claim 15 wherein X is methyl and n is 1.
26. The method of claim 15 wherein X is ethyl and n is 1.
27. The method of claim 15 wherein X is methyl and n is 2.
28. The method of claim 15 wherein X is $CF_3$ and n is 2.
29. The method of claim 15 wherein n is 0.
30. The method of claim 15 wherein the weed herbicide is selected from the group consisting of 2-chloro-2',6'-diethyl-N-(methoxymethyl)acetanilide; 2,3,3-trichloroallyldiisopropylthiocarbamate; 2-chloro-4-ethylamino-6-isopropylamino-1,3,5-triazine; and 2-chloro-2'-methyl-6'-methoxy-N-(isopropoxymethyl)acetanilide.

31. A mixture comprising a herbicidally-effective amount of at least one herbicide and a safening-effective amount of at least one compound having the structural formula:

wherein A is selected from the group consisting of naphthalenyl, tetrahydronaphthalenyl, benzodioxol, and

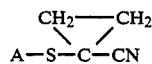

wherein X is independently selected from the group consisting of halogen, haloalkyl, alkyl, alkenyl, alkoxy, alkylthio, alkylcarbonyl, alkylalkenyl, and cycloalkyl; and n is a whole number from 1 through 5.

32. The mixture of claim 31 wherein the herbicide is selected from the group consisting of 2-chloro-2',6'-diethyl-N-(methoxymethyl)acetanilide; 2,3,3-trichloroallyldiisopropylthiocarbamate; 2-chloro-4-ethylamino-6-isopropylamino-1,3,5-triazine; and 2-chloro-2'-methyl-6'-methoxy-N-(isopropoxymethyl)acetanilide.

* * * * *